(12) United States Patent
Chicchetti et al.

(10) Patent No.: US 9,046,609 B2
(45) Date of Patent: Jun. 2, 2015

(54) PORTABLE RADIATION IMAGING SYSTEM

(75) Inventors: Peter M Chicchetti, Coral Springs, FL (US); Michael L Rocha, Sunrise, FL (US); Christopher Duca, Cape Coral, FL (US)

(73) Assignee: Virtual Imaging, Inc., Deerfield Beach, FL (US)

( * ) Notice: Subject to any disclaimer, the term of this patent is extended or adjusted under 35 U.S.C. 154(b) by 235 days.

(21) Appl. No.: 13/388,396

(22) PCT Filed: Nov. 24, 2010

(86) PCT No.: PCT/US2010/058102
§ 371 (c)(1),
(2), (4) Date: Feb. 1, 2012

(87) PCT Pub. No.: WO2011/066461
PCT Pub. Date: Jun. 3, 2011

(65) Prior Publication Data
US 2012/0128127 A1   May 24, 2012

Related U.S. Application Data

(60) Provisional application No. 61/264,525, filed on Nov. 25, 2009.

(51) Int. Cl.
*G01N 23/04* (2006.01)
*H05G 1/10* (2006.01)
(Continued)

(52) U.S. Cl.
CPC ... *G01T 7/00* (2013.01); *A61B 6/00* (2013.01); *A61B 6/4405* (2013.01)

(58) Field of Classification Search
CPC .............................. H05G 1/10; A61B 6/4405
USPC ...................................................... 378/62, 91
See application file for complete search history.

(56) References Cited

U.S. PATENT DOCUMENTS 4,605,959 A * 8/1986 Colbaugh ...................... 348/158
5,608,774 A * 3/1997 Polichar et al. ............. 378/98.8
(Continued)

FOREIGN PATENT DOCUMENTS

CN   1985106559 A   3/1987
WO   2007062181 A2  5/2007

OTHER PUBLICATIONS

SAIC: From Science to Solutions, RTR-4 Portable Digital X-Ray System: Fast Online X-Ray Inspection—When and Where you need it, 2010, pp. 1-6, Science Applications International Corporation.
(Continued)

*Primary Examiner* — David J Makiya
*Assistant Examiner* — Danielle Fox
(74) *Attorney, Agent, or Firm* — Canon USA Inc. IP Division

(57) ABSTRACT

A portable radiation imaging system (10) includes a radiation source (11), a radiation detector (7), a remote trigger unit (17) that activates the radiation source (11) and the radiation detector (7) to initiate an imaging operation, a computing device (13) that receives and processes image data generated by the radiation detector (7), and a universal power box (UPB) (1) operatively connected to the radiation source, the radiation detector, the trigger unit and the computing device. A first wireless link (50) is established between the UPB (1) and the computing device (13), and a second wireless link (60) is established between the trigger unit (17) and the UPB (1). Under the control of the UPB (1), the trigger unit uses the second wireless link (50) to send a control signal to the radiation source (11) to initiate the radiation operation, and the computing device (13) uses the first wireless link (50) to receive image data from the radiation detector (7). The trigger unit (17) can remotely initiate the radiation operation.

12 Claims, 13 Drawing Sheets

(51) Int. Cl.
*G01T 7/00* (2006.01)
*A61B 6/00* (2006.01)

(56) References Cited

U.S. PATENT DOCUMENTS 5,675,472 A * 10/1997 Hamerton-Kelly ...... 361/679.32
2005/0031087 A1* 2/2005 Maschke ...................... 378/196

OTHER PUBLICATIONS

Vidisco Ltd., Vidisco Flat foX-17 & foX-Rayzor Portable a-Si Flat Panel X-ray Inspection Systems, Nov. 2006, pp. 1-6.
English translation of CN1985106559 cited in counterpart Chinese application; Aug. 29, 2014.

* cited by examiner

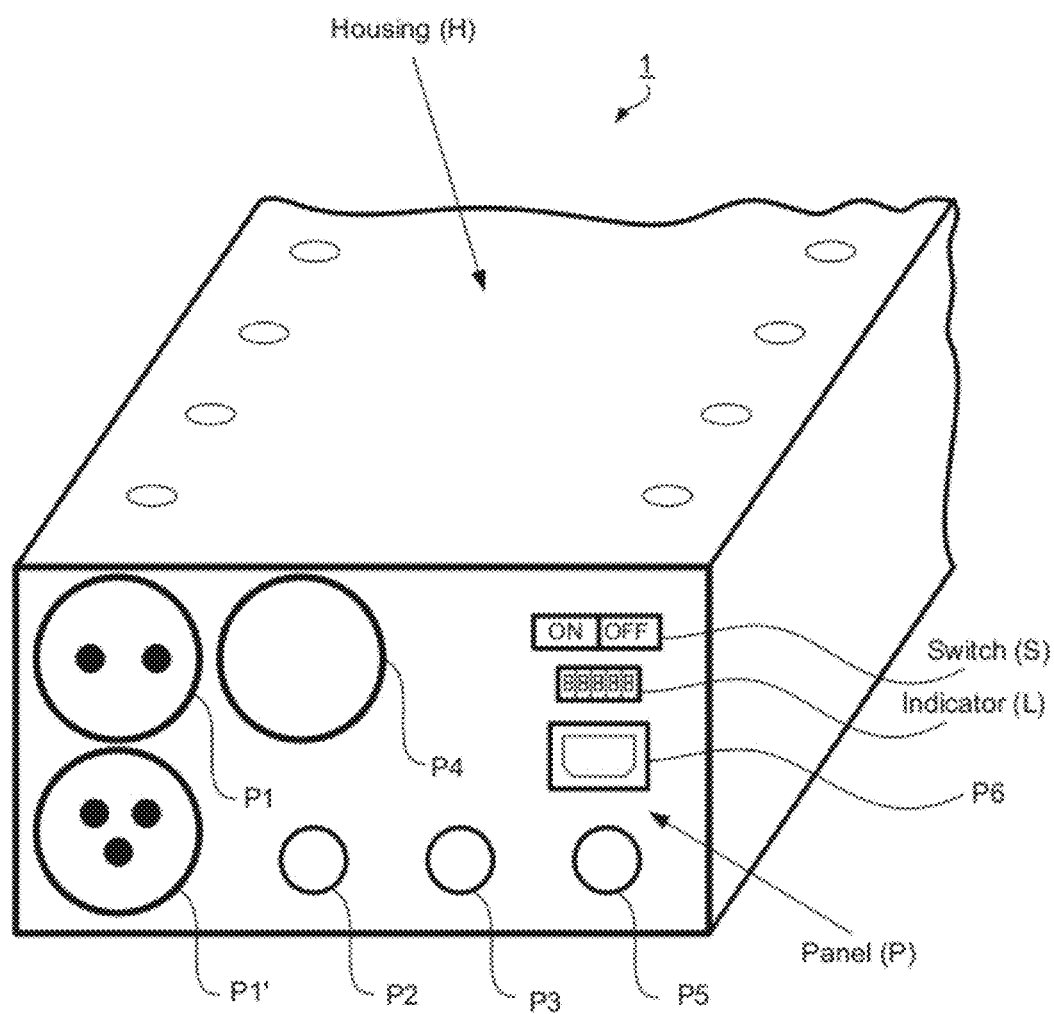

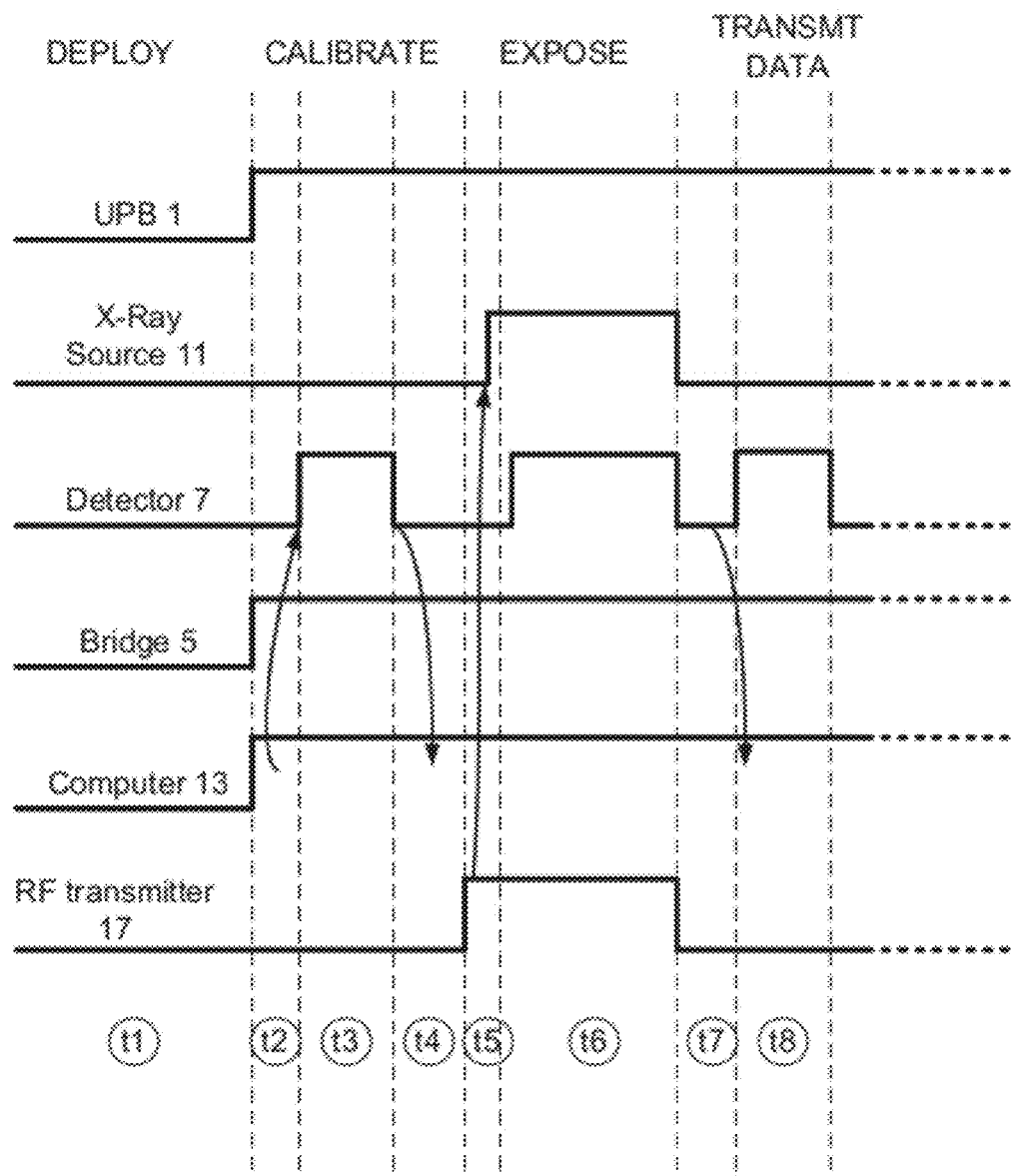

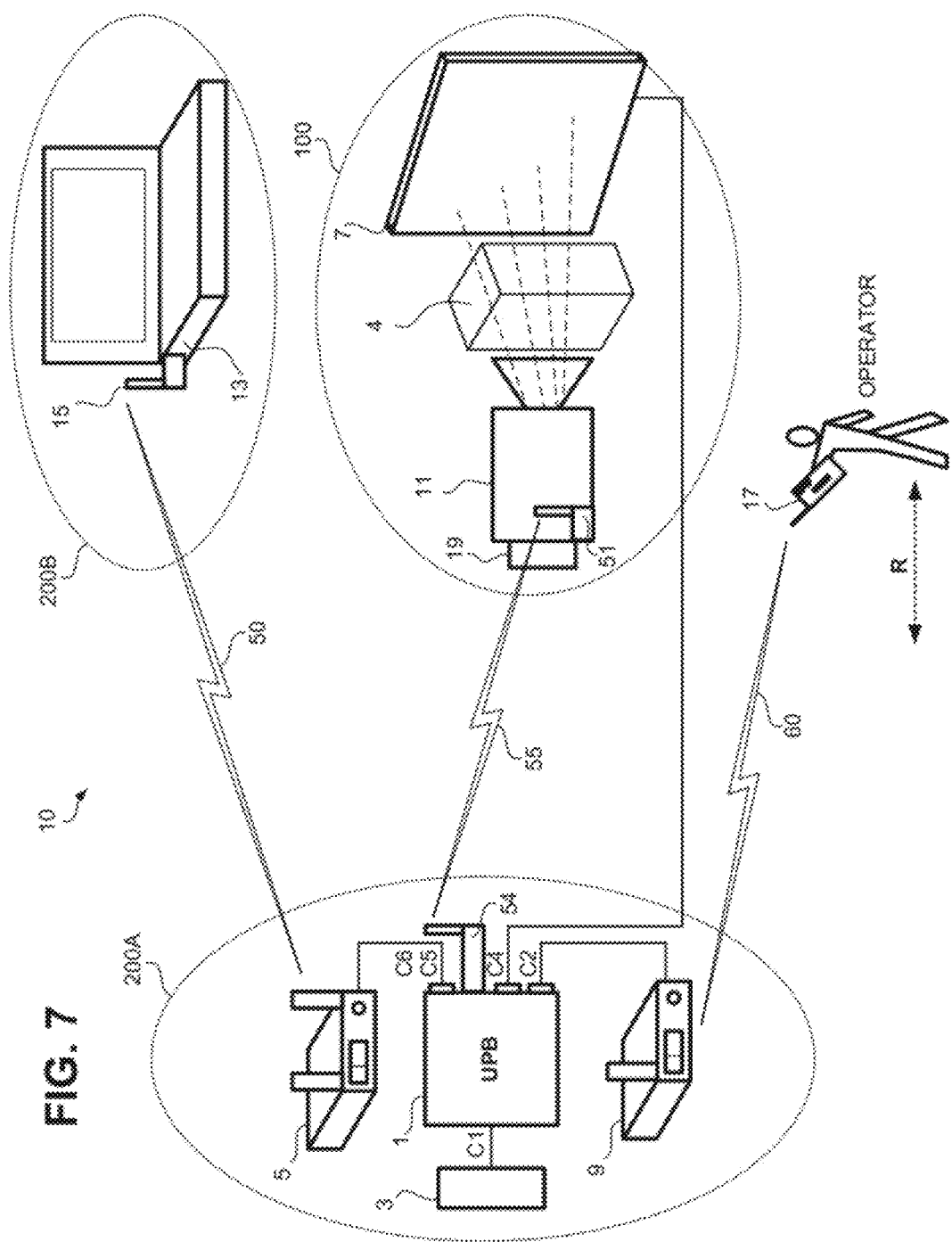

PORTABLE RADIATION IMAGING SYSTEM

CROSS-REFERENCE TO RELATED APPLICATIONS

This application is a U.S. National Stage of International application No. PCT/US2010/058102 filed on Nov. 24, 2010 which claims priority to U.S. provisional patent application Ser. No. 61/264,525 filed Nov. 25, 2009, the disclosures of which are hereby incorporated by reference herein in their entirety.

BACKGROUND OF THE INVENTION

1. Field of the Invention

The present invention relates to radiographic imaging, and more specifically it relates to a portable radiographic imaging system useful for deployment in open-field environments.

2. Description of Related Art

Digital radiography is a form of radiation imaging in which digital sensors are used to detect radiation instead of traditional film cassettes. Digital radiography is rapidly becoming the de facto standard for medical and security imaging as it provides substantial advantages over traditional analog radiographic systems. Not only does digital radiography offer higher resolution and higher quality images with more quantization bits, but it also permits rapid transmission and analysis of captured images.

In a traditional setting, after capturing an x-ray or other radiation-based image, a technician has to develop a film cassette, evaluate the image to ensure that it is readable, and then deliver the image to the correct individual (physician, investigator, screener, etc. . . . ) for diagnosis or analysis. However, with digital radiography, a technician has the ability to capture an image in real-time, immediately evaluate the image (e.g., in a display) to ensure that is readable, and then make it available to any number of individuals by simply uploading it to a computer and transferring it via e-mail, the Internet, or by hardware storage such as a hard drive, flash drive, or memory card.

Digital radiography ("DR") technology is implemented in a number of ways. First, there are systems which are designed to retrofit pre-existing analog imaging devices, whether they are large imaging "rooms" or mobile units. Also known in the art are newer stand-alone mobile or portable digital imaging devices. However, even the most advanced mobile DR devices have encountered serious shortcomings For example, the majority of existing mobile DR units are often quite bulky and are not sufficiently capable of deployment outside of an institutional setting, e.g., hospital, secured building, or security checkpoint. Moreover, even the currently known portable DR systems are limited to be used only in certain environments due to certain constraints.

For example, U.S. Pat. No. 5,608,774 discloses a portable X-ray apparatus applicable to instances where it is necessary to examine or inspect, in a non-invasive manner, a patient, animal, or other living organism; or to examine and inspect, in a non-destructive manner, the contents of a closed package or other container. As described in U.S. Pat. No. 5,608,774, components of the portable DR system are wired together and an operator is required to be present within the immediate premises where an object is to be imaged.

There are instances, however, when it may be unnecessary or undesirable that the operator be present within the premises where the object is to be imaged. One example of when the presence of the operator may be undesirable within the imaging area is when the contents to be inspected by the imaging system may be potentially harmful to the operator; for example when imaging objects that may explode, objects that may be contaminated by nuclear or biologic agents, etc. Another example of when the presence of an operator may be undesired within an imaging area is when the imaging system is being used in covert operations; for example when attempting to detect contraband or illicit materials being transported through certain locations. In the case of covert operations, it may be advantageous that there is no line of sight between an operator of the imaging system and an object or person being imaged. A further example of when the operator of the imaging system may not be present within the imaging area is in telemedicine. Specifically, in the case of telemedicine, an imaging system can be applied, for example, to the military field or a disaster zone, wherein at least the radiation source and the radiation detector can be placed in a field location, while an operating control unit can be placed at a remote location (e.g., a moving vehicle) where a medical professional can receive the images.

In each of the above examples and many other such situations, it would be highly advantageous if the operator could be located remote from the imaging area. Specifically, it would be advantageous if the operator could operate the imaging system while freely moving between predetermined locations. In these instances, secure and reliable transmissions of image data, as well as accurate signaling between the components of the system are paramount to the reliability of such an imaging system.

Accordingly, there exists a need for a lightweight, self-contained, easy to deploy, portable radiation imaging system that is effective for medical, veterinarian, industrial, military, law enforcement, and private security applications that can be safely and reliably used even if an operator of the system is positioned remotely from the location of imaging.

SUMMARY OF INVENTION

The system of the present invention comprises a radiation source, a radiation detector, a universal power box, a power source, a transmitter, a receiver, a bridge, a computing device, and a transceiver. The power source is connected to and provides power to the universal power box. The universal power box is connected to and powers the receiver, the bridge, and the detector. The universal power box is connected to and receives image data from the detector. Additionally, the power box is connected to and transmits this data to the bridge and the bridge transmits the data to the computer device via the transceiver. The aforementioned receiver is capable of receiving a signal from the transmitter which in turn transmits that signal to the universal power box. Thereafter the universal power box sends the signal to the radiation source, initiating irradiation. Accordingly, the object to be imaged is disposed between the radiation source and the detector whereby, after irradiation, the detector acquires the resultant image. The radiation source and the radiation detector are located at a first location; the other components are located at a second or several locations.

BRIEF DESCRIPTION OF THE DRAWINGS

FIG. 3 shows a perspective view of a universal power box (UPB) in accordance with one embodiment of the present invention.

FIG. 4C illustrates a timing diagram illustrating signal synchronization controlled by the universal power box, in accordance with one embodiment of the present invention.

FIG. 7 shows an exemplary arrangement of components of a radiation imaging system in a deployed state, in accordance with another embodiment of the present invention.

DETAILED DESCRIPTION OF EMBODIMENTS

<First Embodiment>

Figure 1:
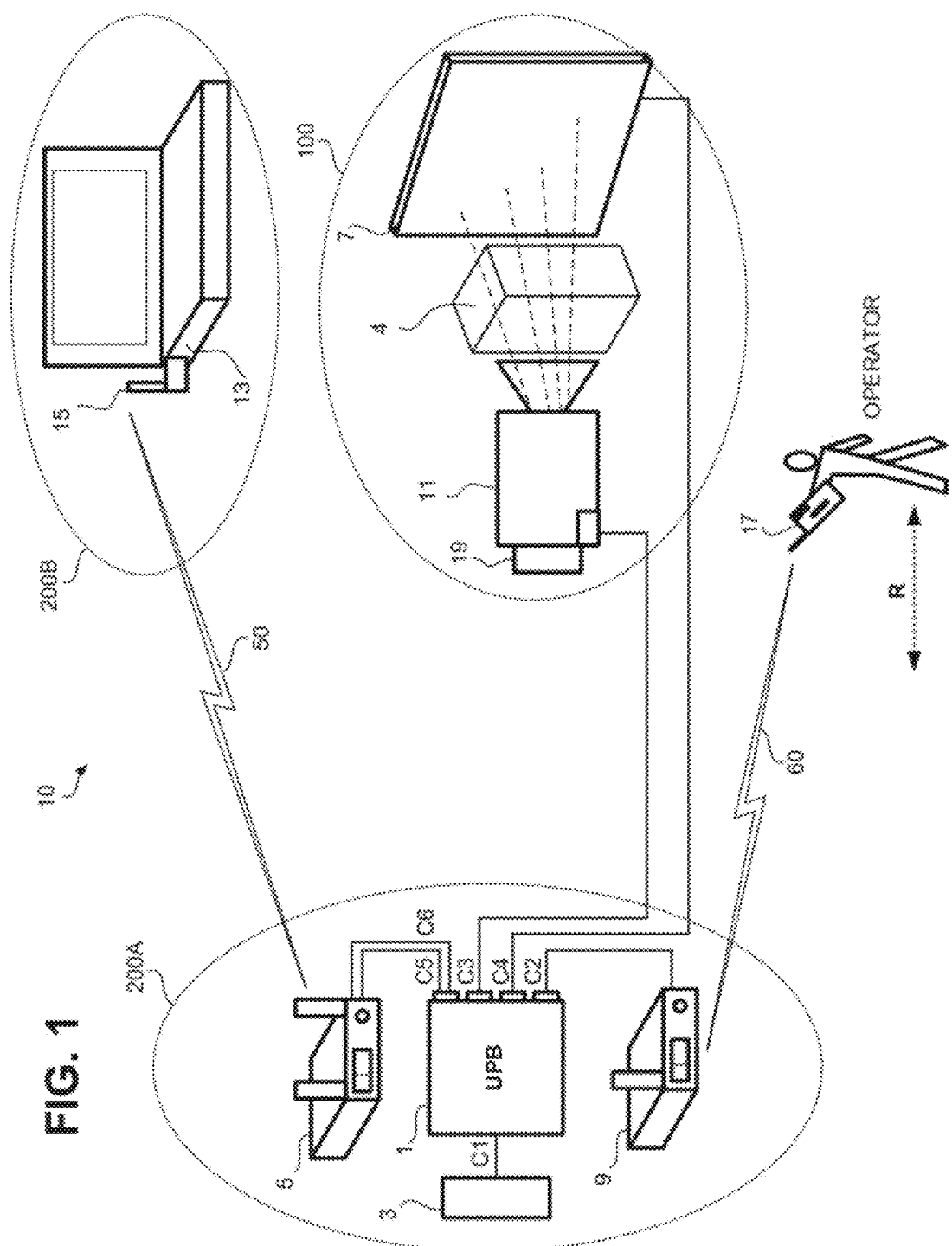
FIG. 1 shows an exemplary arrangement of components of a radiation imaging system in a deployed state, in accordance with one embodiment of the present invention.

FIG. 1 schematically shows an overview of a portable radiation imaging system 10 (also referred to as "system 10") in a deployed state, in accordance with a first embodiment of the present invention. Shown in FIG. 1 are a Universal Power Box ("UPB") 1, a power source 3, a wireless bridge 5, a radiation detector 7, a radio frequency ("RF") receiver 9, and a radiation source 11. Further shown are a computing device 13 including a data transceiver 15, and an RF transmitter 17 being held by an operator of imaging system 10.

As illustrated in FIG. 1, at least the radiation source 11 and the radiation detector 7 may be located at a first location 100, and disposed opposite to each other so as to capture an image of a predetermined object 4. The remaining components of the imaging system 10 may be located at one or more additional locations (200A, 200B . . . ), which can be situated immediately nearby, or remote from the first location. As used herein the term "remote" is intended to indicate a location or device that is physically located at a predetermined distance from another location or device. The predetermined distance can be determined in accordance with a desired application, based on a number of considerations. For example, as illustrated in FIG. 1, the first location 100 can be considered to be remote from the second location 200A or 200B, if the predetermined distance therebetween prevents that radiation emitted from the radiation source 11 interferes with the functionality of UPB 1, wireless bridge 5, or computing device 13.

Accordingly, in this case, it can be said that the predetermined distance may be a function of the distance required to prevent interference between at least two components (e.g., radiation source 11 and UPB 1) of the radiation imaging system 10. In addition, the first location 100 could also be considered remote from a second location 200B, if the predetermined distance therebetween prevents harm to an operator, for example, when imaging a potentially explosive or biological harmful object. Moreover, the first location 100 can also be considered to be remote from the second location 200B, is the predetermined distance therebetween prevents direct line of sight between an object being imaged and the operator of the system.

The first location may be substantially remote from the second location. For example, in a case where the system 10 of FIG. 1 is applied to a telemedicine environment, the radiation source 11 and radiation detector 7 can indeed be located up to several miles remote from the computing device 13 or the RF transmitter 17. Specifically, in a disaster zone, for example, only the radiation source 11, radiation detector 7, and UPB 1 with wireless bridge 5 and RF receiver 9 need to be deployed at a location where a subject is to be imaged. The mobile device 13 and RF transmitter 17 can be deployed at a second location, for example, at medical vehicle. In this manner, medical personnel can operate from the medical vehicle, for example, can remotely perform an imaging operation and immediately receive imaging results via wireless communication. Accordingly, the maximum distance between remote locations may be a function of the distance required to efficiently and securely transmit image data from the radiation detector 7 to the computing device 13. Alternatively, the maximum distance between remote locations may be a function of the distance required to timely and effectively send a control signal (trigger signal) from the RF transmitter 17 to RF receiver 9 over a second wireless link 60. In addition, it should be noted that although FIG. 1 illustrates specific components of the imaging system 10 grouped in a specific first location 100 and second locations 200A or 200B, the arrangement is not limited thereto. As long as at least the radiation source 11 and radiation detector 7 are located in a first location, the remaining components may be located at any number of locations remote from the first location.

In the radiation imaging system 10 of FIG. 1, UPB 1, which is operatively connected to power source 3 via a cable C1, is a multiple-input/multiple-output control unit that is capable of providing an operating voltage (power) and control logic to the components attached thereto. More specifically, UPB 1 includes circuitry for delivering appropriate power to wireless bridge 5, RF receiver 9 and radiation detector 7 via cables C5, C2 and C4, respectively. UPB 1 also includes logic for synchronizing and controlling the interchange of data between RF transmitter 17, radiation source 11, radiation detector 7, and computing device 13. Each of the foregoing components will be now described below in greater detail.

Power source 3 may be a military-grade rechargeable lithium ion battery such as Bren-Tronics® Model No. BB-2590/U. In one embodiment, the power source 3 provides DC voltage in the range of 5-28 V. Alternatively, power source 3 could be an AC source running at between 90-260 Vac. Further, power source 3 could be a conventional chemical DC battery or an external DC source such as a car battery. That is, where feasible, UPB 1 may be connected directly to a DC output of a vehicle or to a DC/AC inverter connected to a vehicle's battery. Further, power source 3 may comprise an array of solar panels or any other power source capable of providing sufficient voltage to UPB 1.

Wireless bridge 5 may be a typical 802.11a/b/g/n capable wireless router as is known in the art. However, for extended range and optimum reliability a high powered (e.g., around 600 mW) router, such as, for example, the EnGenius® Technologies Model No. ECB-36105 may be used. In other embodiments, wireless bridge 5 may be a ruggedized wireless router such as N-Tron® Model No. 702W manufactured by N-TRON Corp. The wireless bridge 5 could be configured to operate over a cellular network or any other network with sufficient bandwidth to meet imaging system requirements. It is understood that wireless bridge 5 is at least capable of transmitting and receiving data over a secure, encoded connection using any encryption means known in the art, including but not limited to, Wired Equivalent Privacy (WEP), Wifi Protected Access (WPA or WPA2) protocols or the like.

Wireless bridge 5 is used to establish a first wireless link 50 with computing device 13 via a wireless transceiver 15. In the present embodiment, the first wireless link 50 is used for transmitting high-resolution and high-quality image data captured by radiation detector 7 to computing device 13. The first wireless link 50 is also used to transmit data related to imaging conditions such as parameters for photographing images, exposure time, identification of other photographic conditions (e.g., still imaging or dynamic imaging), object identification specified by the operator, etc. To that end, the first wireless link 50 may be implemented as a wideband, high-speed, connection link capable of reliably transmitting data-intensive, high-resolution and high-quality image data between UPB 1 and computing device 13. Accordingly, the first wireless link 50 between wireless bridge 5 and computing device 13 can be also referred to as an "image-transfer link".

The above-mentioned first wireless link 50 established between wireless bridge 5 and wireless transceiver 15 could be replaced or duplicated by any other known wired or wireless communication means such as "CAT-5" Ethernet® cable, telephone cable, fiber optic cable, Bluetooth®, or other known network. For example, a network may be formed as a digital wireless wide area network (WWAN), based on architectures such as Global System for Mobile Communication (GSM), IS-136 TDMA-based Digital Advanced Mobile Phone Services (DAMPS), Personal Digital Cellular (PDC), IS-95 CDMA-based "cdmaOne" System, CDMA2000, General Packet Radio Service (GPRS) and broadband wireless architecture such as W-CDMA and Broadband GPRS, Mobitex, HSDPA, 3G, 4G. In addition, a physically wired connection may be established instead of, or in addition to, the first wireless link 50.

One reason for replacing the first wireless link 50 with a wired connection may be to avoid interference of data transmission, which may occur under heavy radiation and/or noisy environment backgrounds. Alternatively, a wired connection can be implemented in addition to the first wireless link 50, as a redundant or complementary communication channel, to expedite transmission of the high-resolution and high-quality image data generated by radiation detector 7 and transmitted under control of UPB 1 to computing device 13.

Referring still to FIG. 1, computing device 13 may comprise, without limitation, a standard laptop computer, a ruggedized laptop computer (such as Panasonic® Toughbook® Model No. CF 19), a standard desktop computer, a handheld device such as a personal digital assistant (PDA), or an ultramobile personal computer (UMPC). Wireless transceiver 15, which communicates with wireless bridge 5 in the manner described above, may be an internal adapter built into computing device 13 or it may be an external device operatively connected to computing device 13 through a universal serial bus (USB), IEEE 1394, serial, parallel, or other like connection known in the art. In one such example, transceiver 15 may be a high-powered WiFi® enabled device capable of transmitting at up to 600 mW of power over standard wireless protocols, such as 802.11a/b/g/n or the like. Computing device 13 runs imaging control software R (not shown), which processes the imaging data and controls the majority of the functions of the system 10. One example of software R is Canon® CXDI Control Software, which may run on the Microsoft® Windows platform or another operating system known in the art.

Radiation detector 7 (also referred to as "detector 7" for simplicity) is a light-weight, compact and portable detector capable of detecting electromagnetic or particle radiation emitted from radiation source 11. Currently, there exists a large selection of portable radiation detectors including CR (computed radiography) cassettes and digital flat panel detectors (FPD) that may be applicable to the imaging system 10. Radiation detector 7 may be implemented as a static or dynamic digital imaging detector such as, without limitation, Canon® digital radiography detector CXDI-50C, CXDI-50G or CXDI-60G. Moreover, radiation detector 7 may be implemented as a static and dynamic digital imaging detector capable of performing still radiation imaging, dynamic radiation imaging, or a combined imaging procedure in which still and moving images may be obtained. During operation, radiation detector 7 is synchronized with the radiation source 11, such that when radiation source 11 irradiates a predetermined object 4 with predetermined amounts of radiation, radiation detector 7 detects the radiation passing through the object 4 and generates image data corresponding to an image of the object.

Radiation source 11 is connected to UPB 1 via cable C3 and is activated by a trigger signal 55 delivered thereto over cable C3. Radiation source 11 can be, for example, a lightweight x-ray generator that is powered by its own removable battery pack 19 and generates x-ray radiation based on predetermined radiation imaging parameters. Commercially available x-ray sources that produce x-ray pulses of very short duration (e.g., in the range of 60 nanoseconds) can be applicable. One example of radiation source 11 includes the Golden Engineering's Model XRS-3 manufactured by Golden Engineering Inc., of Centerville, Ind. Another example of radiation source 11 may be the Poskom Model No. PXM-40BT for human use or PXM-20BT for veterinary use, both models manufactured by Poskom Co. Ltd. of Goyang, South Korea. It will be understood, however, that any similar x-ray source or other like radiation source, such as a neutron generator or a gamma-ray source, known in the art may employed as the radiation source 11, depending on the specific application and detector compatibility.

RF trigger 17 is an example of a mobile (portable) trigger unit that serves to emit a control or trigger signal (control/trigger data), such that the radiation source 11 may initiate a radiation emission operation by emitting predetermined amounts of radiation towards an object 4. More specifically, as illustrated in FIG. 1, RF transmitter 17 is a portable trigger unit that can be used by an operator to issue a control signal over the second wireless link 60, even if the operator is moving in a direction R. That is, RF transmitter 17 can be advantageously used to allow an operator to freely move to any desired location, so as to safely and remotely initiate an imaging operation by emitting control signal over the second wireless link 60. The control signal emitted from the RF transmitter 17 under the control of the operator is received by the wireless receiver 9 and is thenceforth sent to radiation source 11 under the logic control of UPB 1. To that end, upon receiving the control signal via RF receiver 9, UPB 1 (based on logic circuitry built therein) issues a synchronized signal to radiation source 11 and radiation detector 7, so that radiation emission can be initiated and image data can be detected, respectively in that order.

RF transmitter 17 is a long range, multi-channel, digitally encoded RF transmitter such as Model No. XT-4H manufactured by Linear® Corporation of Carlsbad, Calif. The RF transmitter 17 in this embodiment has manually operable switches including a trigger switch for sending a control signal over the second wireless link 60, which is described in more detail later. The manually operable switches can be operated by a system user (operator) separately from a keyboard or other controls of the computing device 13. Like the RF transmitter 17, RF receiver 9 is a long range, multichannel, digitally encoded RF receiver such as Model No. XR-4 also manufactured by Linear® Corporation. As described in detail below, when receiver 9 is triggered (for example, by the control signal emitted from RF transmitter 17), the receiver 9 is capable of sending a "switched" trigger signal to a remote device, such as radiation source 11, under the control of UPB 1. In the present embodiment, RF transmitter 17 and receiver 9 are intended to operate as "switched" radio frequency controllers, however, it will be understood by persons skilled in the art that any like transmitter/receiver combination that is capable of providing a switched signal to a remote device may be equally suitable. RF transmitter 17 is intended to operate as a remote hand switch for radiation source 11, whereby RF transmitter 17, when activated by the operator, sends a radio signal to RF receiver 9 which in turn passes the signal to UPB 1, which further in turn sends a triggering signal to radiation source 11 in order to initiate an imaging operation—as described more in detail in reference to FIG. 4C.

Because the control signal from RF transmitter 17 must be accurately timed to trigger the radiation source 11, and in turn the trigger signal must be timely synchronized with the detection process of radiation detector 7, the timing of the trigger signaling is an important aspect of the present embodiment. In other words, the control signal path (or any part thereof) formed by RF transmitter 17 to RF receiver 9 to UPB 1 and on to radiation source 11, which is used for delivering time-critical data such as a control signal from RF transmitter 17 to radiation source 11, will be referred to as a "time-critical" link. Incidentally, information sent over the time-critical link will be referred to as "time-critical" data.

In the above configuration, it should be noted that the control signal emitted from the RF transmitter 17 is used by UPB 1 to send a synchronized trigger signal to radiation source 11 and initiate radiation emission from radiation source 11. In addition, the control signal may also be used by UPB 1 to initiate a radiation detection operation of the radiation detector 7, and subsequent acquisition of image data from radiation detector 7. A detailed discussion of the synchronization and timing implemented by the logic circuitry of UPB 1 is described below in reference to FIG. 4C.

Figure 2:
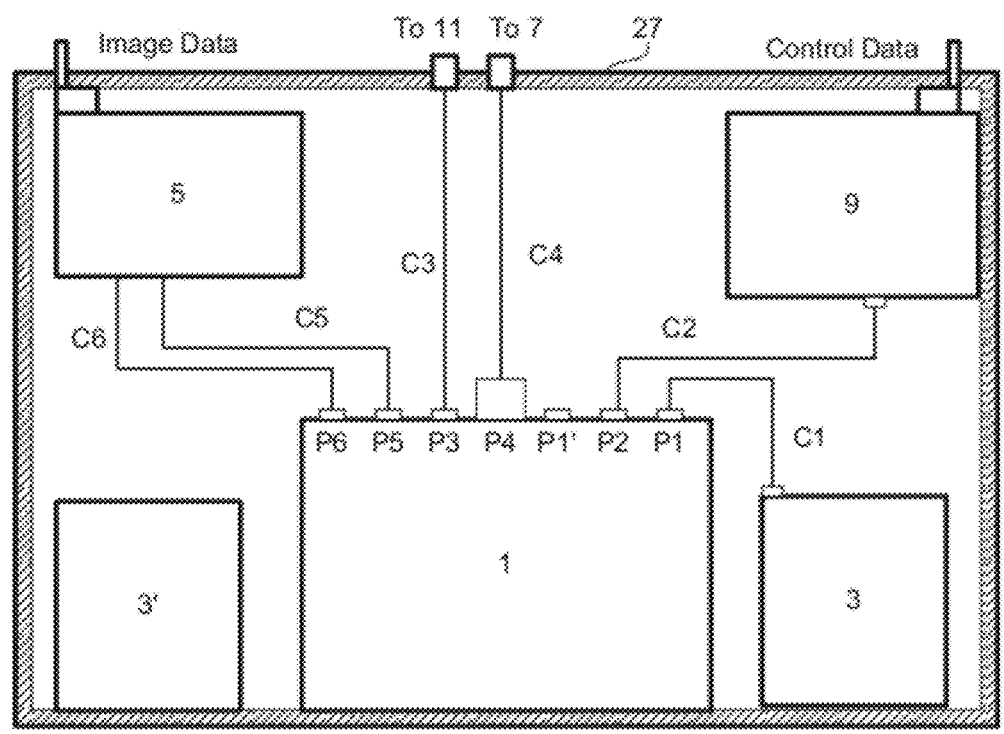
FIG. 2 shows certain components of the imaging system assembled on a board or panel in accordance with one embodiment of the present invention.

FIG. 2 illustrates one exemplary arrangement in which UPB 1, power source 3, wireless bridge 5, receiver 9, and a spare power source 3' are mounted onto a board or panel 27 in order to keep the system self-contained and organized. Shown in FIG. 2 are UPB 1 connected to power source 3 via cable C1; wireless bridge 5 connected to UPB 1 via cables C5 and C6; RF receiver 9 connected to UPB 1 via cable C2; UPB 1 connected to radiation detector 7 via detector cable C4; and UPB 1 connected to radiation source 11 via cable C3. UPB 1 is powered by power source 3 over cable C1 which in turn allows UPB 1 to provide power (appropriate operative voltage) to the various components attached thereto.

Cable C2 is a multi-function cable connected between RF receiver 9 and UPB 1. Cable C2 is used for providing power to RF receiver 9 from UPB 1, and for sending a switched signal from RF receiver 9 to UPB 1. Thus, the switched signal from RF receiver 9 goes through UPB 1, and is passed through cable C3 to radiation source 11, in order to control the emission of radiation from radiation source 11.

Detector cable C4 is a multi-function cable connected between radiation detector 7 and UPB 1. Cable C4 is used for providing power from UPB 1 to radiation detector 7, and also for permitting two-way data transfer between the radiation detector 7 and UPB 1. Image data received at UPB 1 from radiation detector 7 is passed over cable C6 to wireless bridge 5. UPB 1 also powers the wireless bridge 5 over cable C5. In one embodiment, cable C6 may be a standard CAT-5 Ethernet® cable or may be any other suitable connection that it is compatible with wireless bridge 5.

Accordingly, as described above, UPB 1 is a multiple-input/multiple-output control unit that is capable of providing power and control logic to system components attached thereto, as well as permitting processing and transmission of data therethrough. More specifically, one of the challenges in providing a light-weight and easy to deploy portable radiation system 10, as described herein, is the integration of the several components into one or more small modular packages that can be safely transported and rapidly deployed. Most modern imaging and communications equipment include integrated circuits (ICs) that have different types of input/output (IO) interfaces to communicate with other integrated circuits. The interfaces often require different power supply voltage levels, such as 12V, 5V, 3.3V, 2.5V, 1.8V, etc. to support a number of different peripheral devices. Accommodating the entire possible range of supply voltages from high voltage to low voltage within a single package represents a significant design and manufacturing challenge because such voltages must be properly distributed and buffered to ensure proper operation and protection of the devices connected thereto. In the present embodiment, UPB 1 has been designed to meet such requirements.

FIG. 3 is an exemplary partial perspective view of the universal power box UPB 1. Shown are a front panel P and a housing H. Front panel P includes an input port P1 for inputting direct current (DC) and an input port P1' for inputting alternate current (AC) into UPB 1. If power source 3 is a DC source, cable C1 is connected to port P1. Alternatively, if power source 3 is an AC source, cable C1 is connected to port P1'. UPB 1 also includes connecting ports P2, P3, P4, P5 and P6 configured as follows. Cable C2 is connected to port P2, powering receiver 9 and permitting signal transfer from receiver 9 to UPB 1. Cable C3 is connected to port P3, transmitting a switched signal (trigger signal) to radiation source 11. Detector cable C4 is connected to port P4, powering radiation detector 7 and transmitting image data from radiation detector 7 and UPB 1 and image information data from UPB 1 to radiation detector 7. Cable C5 is connected to port P5, and is used for powering the wireless bridge 5. Cable C6 is connected to port P6, and is used for transmitting data from UPB 1 to wireless bridge 5 and vice versa. Power switch S turns UPB 1 on and off. Finally, UPB 1 may include a visual (e.g., LED display) status indicator L for informing of an operational state of UPB 1 to a user thereof.

Figure 4A:
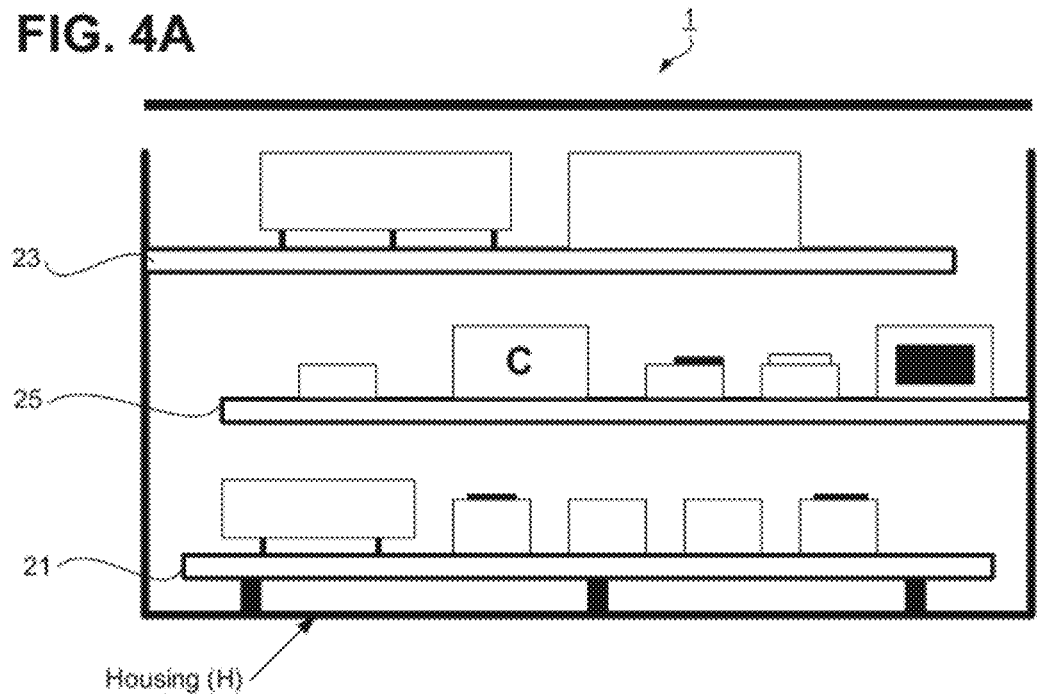
FIG. 4A illustrates an exemplary arrangement of floating-rail boards included the universal power box.
Figure 4B:
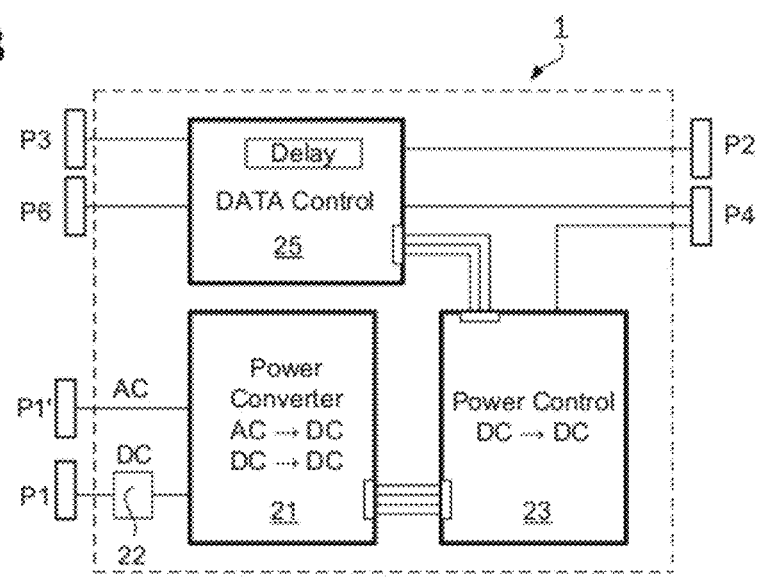
FIG. 4B illustrates a functional diagram and port connections for the floating-rail boards included in the universal power box.

FIG. 4A is a plane side view of an exemplary distribution of floarign rail boards that contain thereon the power and logic circuitry of UPB 1. FIG. 4B is a block diagram exemplifying, in functional blocks, how the boards are used for power distribution and logic signal control. Shown are a bottom power board 21, top power board 23, and a logic interface board 25. In this embodiment, a DC input coming from power source 3 can be connected to port P1 and terminates on bottom power board 21, generating the input voltage for UPB 1. In addition, an AC input from an available AC outlet can be connected to port P1'. Board 21 is provided with AC/DC converter circuitry which is capable of generating DC voltage in the range of 5-28 Vdc from the AC input. The voltage in the AC input may range from 85 to 265 Vac. Accordingly, if it is desired to power UPB 1 with AC, the system may be readily compatible with virtually any AC source, in addition to a DC power source. To that end, the DC input terminal may be diode ORed to the AC input at the output side of AC/DC converter. The ORed configuration allows for the implementation of power source 3 (illustrated in FIG. 1) in the form of on an AC input, a DC input, or a combination of both.

Additionally, board 21 may be provided with at least one, but preferably more, AC filters which suppress any RFI (radio frequency interference) emissions or other undesirable noise produced by the power supply or circuitry thereof. Board 21 may also have one or more DC-to-DC converters capable of stepping down the input voltage to a plurality of different DC outputs to power the components attached to UPB 1. For example, board 21 provides at least a 24 Vdc output to power the wireless bridge 5, and a 5 Vdc output to power the RF receiver 9, among others. Accordingly, board 21 has one or more connectors which are coupled to the front panel ports (e.g., P2, P5) shown in FIG. 3 and described above. Board 21 is also provided with a low-voltage disconnect circuit 22 that is capable of sensing the voltage level of the DC power source and shutting off the aforementioned DC-to-DC converters if the DC input voltage drops below a user-selected minimum threshold.

The top power board 23 has one or more DC-to-DC converters which are connected to board 21 and are powered by DC voltage coming from board 21. The DC-to-DC converters on board 23 are used in conjunction with one or more terminal regulators to step down the input voltage in order to power the radiation detector 7 and other components. Power boards 21 and 23 can also have trim potentiometers adjacent to each output stage in order to set the required voltages depending on the requirements of the components, e.g., wireless bridge 5, receiver 9, and radiation detector 7.

Interface board 25 is connected to and powered by one of the DC-to-DC converters located on top power board 23. In one embodiment, at least part the connectors that form ports P2, P3, P4 and P6 for connecting to receiver 9 (cable C2), radiation source 11 (cable C3), radiation detector 7 (cable C4), and wireless bridge 5 (cable C6), respectively, are connected to interface board 25. Interface board 25 comprises a chipset C that is capable of processing image data received from radiation detector 7 over cable C4 and passing the received image data to wireless bridge 5. Specifically, interface board 25 receives image data from radiation detector 7 in a proprietary format. For ease of transfer, chipset C processes the proprietary format into a format (e.g., Ethernet® format) acceptable for transmission to wireless bridge 5 and computer device 13. That is, interface board 25 processes and passes the image data through to wireless bridge 5 via cable C6 (e.g., Ethernet® cable), so that wireless bridge 5 can transfer the image data to computing device 13 over first wireless link 50. Interface board 25 also controls, processes, and passes through the switched signal coming from receiver 9, in order to trigger radiation source 11. As described below, interface board 25 also includes triggering logic and timing synchronization that prevents radiation source 11 from being triggered by receiver 9 until radiation detector 7 is in a "ready" state. It is understood that the configuration of ports P1 through P6 of board 21, board 23, and interface board 25 with respect to panel P may vary as a matter of design choice depending on, for example, the power requirements and communication capabilities of the components selected. For example, alternative configurations can be designed based on the type of components selected to implement each of radiation detector 7, bridge 5 or RF receiver 9.

FIG. 4C illustrates one possible configuration of the timing logic to be controlled by logic circuitry built in UPB 1. Specifically, as illustrated in FIG. 4C, during a period t1, the portable imaging system 100 is deployed and components thereof are properly connected (setup). After deployment and setup, during a period t2, the computing device 13 and UPB 1 are powered ON (high signal); at substantially the same time (during period t2), power is supplied from UPB 1 to components attached thereto; in particular, wireless bridge 5 and RF receiver 9 are powered ON. Once the wireless bridge 5 and the computing device 13 are powered ON, the wireless bridge 5 establishes communication with computer 13 via transceiver 15 (still during period t2). Once communication is established between UPB 1 and computing device 13 (via first wireless link 50), computing device 13 issues a calibration signal to detector 7. Detector 7 is calibrated (or reset) during a period t3. Once calibrated, detector 7 sends a "ready" signal to computing device 13 via wireless bridge 5, during a brief transition period t4. Immediately, upon receiving the ready signal at computing device 13, the user knows that the detector is ready to receive radiation and proceeds to activate RF transmitter 17 (trigger unit). A control signal is sent from the RF transmitter 17 to radiation source 11—under the logic control of UPB 1—via the second wireless link 60 (time-critical link). That is, until and unless a ready signal is received from detector 7, UPB 1 will prevent the control signal (or trigger signal) from being delivered to radiation source 11. In this manner, once the detector 7 is calibrated and ready, the operator can move away from computing device 13 and initiate an imaging operation even when not present at the imaging location. As discussed above, there may exist several instances where the operator may need to move away from the computing device 13.

Referring back to FIG. 4C, during a period t5, when the operator activates RF transmitter 17 and UPB 1 recognizes that the radiation detector 7 is ready, UPB 1 forwards the trigger signal to radiation source 11. Upon receiving the trigger signal, the radiation source 11 initiates a radiation emission operation, and substantially at the same time, detector 7 initiates a radiation detection operation. Radiation exposure is preformed during a period t6, in accordance with predetermined image requirements. Once radiation exposure is ended, during a brief transition period t7, transmission of the image data from radiation detector 7 to computing device 13 takes place via wireless bridge 5 under control of UPB 1. More specifically, even before the image data is completely transmitted to computing device 13, the radiation detector 7 can start a reset operation during a period t8, for example, when a subsequent trigger signal is issued from RF transmitter 17 via the second wireless link 60. In this manner, the image data is can still be delivered to computing device 13 via the above described first wireless link 50, even if a reset operation is started by RF transmitter 17 via the second wireless link 60. Accordingly, for purposes of this description, the second wireless link between transmitter 17 and receiver 9 will be designated herein as a "time-critical link".

In the first embodiment, the second wireless link 60 between RF transmitter 17 and receiver 9 have a maximum communication range of up to 10 miles, however this range shall not be considered limiting as the range will depend on the capabilities of the transmitter/receiver combination. Advantageously, as described above, when system 10 of the present embodiment is designed with the first wireless link 50 and second wireless link 60, an operator can freely move with a hand switch RF transmitter 17 and decide when to initiate an imaging operation or reset such operation should such be required.

Figure 5:
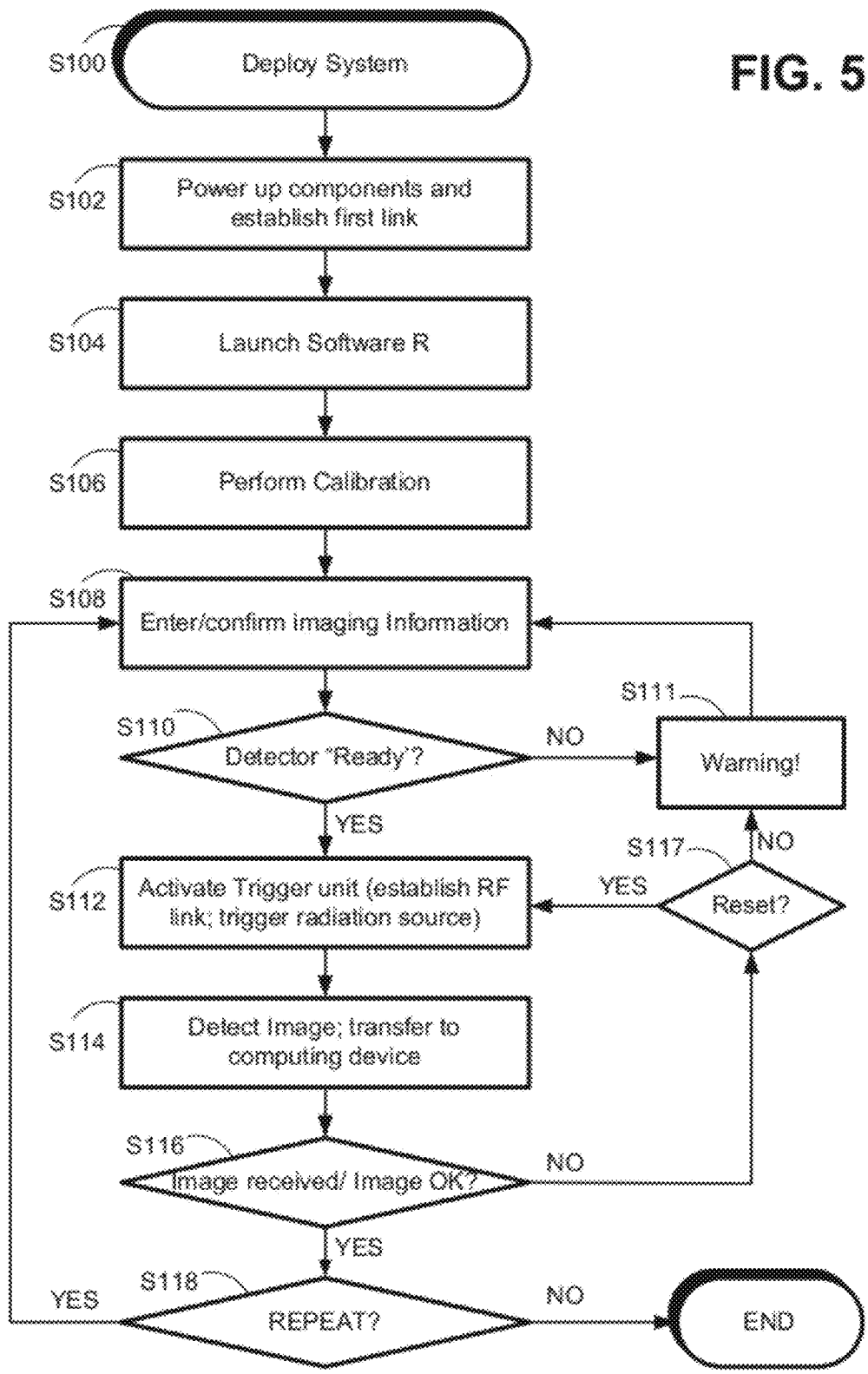
FIG. 5 illustrates an exemplary flow process of a deployment and imaging method, in accordance with at least one embodiment of the present invention.

FIG. 5 illustrates exemplary steps of a deployment and imaging method in accordance with at least one embodiment of the present invention. First, at step S100, the system components are unpacked from carrier 29 and deployed in predetermined locations as convenient. At least radiation source 11 and radiation detector 7 must be deployed at a first location where the object of interest is located. That is, the location where object to be imaged (e.g. a tire, piece of luggage, human body or part thereof, etc. . . . ) is disposed is designated herein at a first location (e.g., location 100 in FIG. 1). UPB 1 and components attached thereto, i.e., power source 3, wireless bridge 5 and RF receiver 9, are set up at a second location which may be within the immediate vicinity of (or remote to) the object to be imaged. As long as radiation from radiation source 11 or environmental conditions do not interfere with the operation of UPB 1, UPB 1 may be deployed at any location—including the first location. Deployment of UPB 1 may involve simply unloading panel 27 from its respective container, placing it within the chosen location, and securing connections with radiation source 11 and radiation detector 7.

Computing device 13 (with transceiver 15 built-in or connected thereto) may be set up at a third location 200B which could be a remote place at a predetermined distance away from the first location 100 and/or second location 200A, depending on the relative range capabilities of the transmitter/receiver and transceiver/bridge connections. Of course, the third location 200B may be in the immediate vicinity of the first and second locations, if preferred by the system operator(s). Alternatively, as discussed above, computing device 13 may be located in a remote location miles way from the first location, e.g., where images of the object are desired.

At step S102, after the operator ensures that UPB 1 is securely connected to radiation source 11, radiation detector 7, wireless bridge 5 and RF receiver 9 via all the requisite connections (cables C1-C6), UPB 1 is powered on by operating on switch S. Accordingly, wireless bridge 5, radiation detector 7, and receiver 9 are now powered ON and active. Next, or at substantially the same time, the operator also boots up computing device 13. Thereafter, a secure two-way communication link (first wireless link 50) is established between UPB 1 and computing device 13 by wireless bridge 5 and wireless transceiver 15, respectively. At step S104, after confirming that the first wireless link 50 has been established, an operator launches software R in computing device 13. At this point, based on the logic of software R, computing device 13 is capable of communicating with and controlling the radiation detector 7 via wireless bridge 5 over the pass-through connection in UPB 1.

At step S106, before acquiring and processing an image, radiation detector 7 should be calibrated by executing a calibration sequence implemented by software R. In that sense, calibration instructions are sent from computing device 13 to radiation detector 7 over the aforementioned first wireless link 50 between computing device 13 and UPB 1 (i.e. transceiver 15/bridge 5). After calibration, the system is readied for imaging. It will be understood that the calibration procedure need only be performed periodically, for example at deployment, and is not necessary to perform during each "normal" operation of the system. Next, at step S108, on the graphical user interface (GUI) of software R, an operator enters image information, i.e. patient/object name, identification number, date, time, etc. . . . , and then selects the desired anatomy or object to be imaged.

At step S110, the operator waits for verification that radiation detector 7 is ready to initiate a radiation detection operation (i.e., is ready to capture an image). A detector "ready" signal can be delivered to the computing device 13, as described above, in reference to FIG. 4C. More specifically, radiation detector 7 sends a "ready" signal to UPB 1 over cable C4 and interface board 25 of UPB 1 processes the "ready" signal and then passes it through to wireless bridge 5 over cable C6, which in turn communicates the ready status to software R over the aforementioned first wireless link 50 between wireless bridge 5 and transceiver 15. When interface board 25 of UPB 1 processes the ready signal, the chipset C of board 25 can, for example, clear a "trigger" flag indicating that imaging operation can now be started. Unless and until the "ready" signal is received, the logic control built into interface board 25 of UPB 1 will prevent receiver 9 from triggering the radiation source 11. This assures that radiation source 11 is not unnecessarily or excessively activated, thus minimizing radiation dosing and conserving power.

At step S110, if the detector ready signal is not received by the operator (NO at step S110) within a predetermined time, computing device 13 may determine a reason why the radiation detector 7 is not ready and may issue a warning to the operator, e.g., via a GUI of the computing device 13, at step S111. For example, computing device 13 may determine that the first wireless link 50 does not comply with predetermined data transmission requirements, such as a minimum bandwidth, a maximum distance, noise threshold or the like. Alternatively, UPB 1 may send to computing device 13 an indication that a particular cable (e.g., one or more of cables C1-C6) has been accidentally disconnected. Further, in alternative, computer device 13, based on the imaging information entered at step S108, may determine that either the radiation source 11 or radiation detector 7 is not appropriate for imaging the object of interest. In either of the above scenarios, after issuing the warning at step S111, the process returns to step S108 where imaging conditions are confirmed or changed; and the operator waits for the detector "ready" signal at S110.

Once the ready status has been verified (YES at step S110), the process advances to step S112. At step S112, the operator activates RF transmitter 17 thereby signaling receiver 9 to send a switched signal to UPB 1 over cable C2; in turn, interface board 25 of UPB 1 passes the switched signal to source 11 via cable C3, thereby activating radiation source 11. Radiation source 11 initiates a radiation emission operation and irradiates the object with predetermined amounts of radiation. Substantially simultaneously (see FIG. 4C) radiation detector 7 initiates a radiation detection operation, thereby generating image data. Thereafter, at step S114, the image data generated at radiation detector 7 is sent to UPB 1 over cable C4. The interface board 25 of UPB 1 processes the data and passes it through to wireless bridge 5 via cable C6. Computing device 13 receives the image data from wireless bridge 5 via transceiver 15, and software R processes the received image data to produce an image.

At step S116, the operator verifies (evaluates) image quality of an obtained image. More specifically, at step S116, a determination can be made whether or not an image has been received within a predetermined time, and whether the received image is of an appropriate quality. If an image is not received within the predetermined time, or if the image quality of a received image is not appropriate (NO at step S116), the flow process advances to step S117.

At step S117, the operator is given an opportunity to "reset" the image acquisition process. Specifically, if the operator decides to reset the image acquisition process (YES at step S117), for example, because an image has not been received within a predetermined time, or because the received image is not of appropriate quality, the process advances to S112, where the operator again activates the RF transmitter 17 initiate anew the activation of the radiation source 17 and detector 7. The reset operation described herein has also been described with reference to FIG. 4C above. Returning now to step S117, if the operator does not decide to reset the image acquisition process (NO at step S117), the flow proceeds to step S111. At step S11, the system may issue a waning (or recommendation) to the operator, for example, as in the manner described above with respect to step S111. From step S111, the process immediately returns to step S108 so that the operator may enter new imaging information or confirm the previously entered information.

Returning now to step S116, if an image has been received within a predetermined time at computing device 13 and the evaluation of the image quality is positive (YES at S116), the system can then save the image to an internal memory of the computing device 13 or alternatively to an external storage device. Of course, the images acquired by software R are in a digital format and can easily be transferred electronically over the Internet, via e-mail or through hardware storage means such as, for example, a hard drive, flash drive, or memory card. At step S118, a decision is made of whether to repeat the imaging process or not. If no more images are desired (NO at S118), the process ends. Alternatively, the process returns to step S108, where imaging information is confirmed or new imaging information is entered. That is, to acquire additional images, the process of FIG. 5 is repeated starting at step S108.

As stated at the outset of the present disclosure, there exists a need for a lightweight, self-contained, easy to deploy, portable radiation imaging system that is effective for medical, veterinarian, industrial, military, law enforcement, and private security applications that can be safely and reliably used even if an operator of the system is positioned remotely from the location of imaging. The foregoing description, in which a portable trigger unit (e.g., RF transmitter 17) has been described, may suffice to satisfy and solve the above-mentioned needs of industrial, military, law enforcement, and private security applications.

However, for medical and veterinarian applications, U.S. federal safety regulations require that radiation from a radiation source (e.g., x-ray generator) can only be emitted for the minimum amount of time required to obtain an appropriate image and only at the exact time required (e.g., when a patient is ready and in the appropriate position). To satisfy such safety regulations, a so called "dead-man" switch has been conventionally incorporated into the control circuitry of the radiation source. This means that the operator can control the exposure manually and will not permit radiation emission from the radiation source unless the dead-man switch is activated and held by the operator throughout the exposure operation.

In addition, it is common practice in medical imaging (human or veterinarian) that an X-ray source (generator) must be synchronized with an X-ray detector (detector), so that the generator irradiates the detector at the precise time when the detector is ready to receive a radiation. The generator, however, requires around 800 milliseconds of preparation time (prep period) to be ready to emit radiation. This prep period is required to boost the rotor (tube) for appropriate exposure; accordingly this operation may be referred as "a radiation preparation operation". In contrast, modern DR x-ray detectors require around 300 milliseconds to be ready (ready period) to detect radiation. This ready period is required, for example, to release the exposure contact once an exposure request is received or to reset previous charges in pixels of the detector. Accordingly, a detector requires a ready period to perform "a detection preparation operation". It is, therefore, desirable to synchronize the generator and the detector, so that exposure (i.e., radiation emission from the generator) begins as close as possible to the time when the detector is ready. In the above example, in order for the detector to be ready to detect radiation substantially simultaneously with the time at which the generator starts emitting radiation, the detector should start its detection preparation operation 500 milliseconds later than the generator has started its prep operation. That is the detector is delayed with respect to the detector by a delay period of 500 milliseconds.

In accordance with at least one embodiment of the present invention, it is possible to implement the dead-man switch concept in the RF transmitter 17, and to communicate to the operator of a time when the radiation detector 7 is ready to initiate a radiation detection operation. More specifically, in the foregoing description of the present application, when the radiation detector is ready, a "ready" signal is delivered to computing device 13, whereby an operator of RF transmitter 17 acts thereon and issues a trigger or control signal to the radiation source 11. UPB 1 implements trigger or control signal synchronization. In an alternate embodiment, however, it is possible to configure RF transmitter 17 as the so called "dead man" switch. For example, RF transmitter 17 can be implemented as a single throw double-pole switch that can be activated by the operator in accordance with a "ready" status of the radiation detector 7. Moreover, it is possible to implement RF transmitter 17 as a two-way communication device that can wirelessly communicate with UPB 1, so that RF transmitter 17 can send and receive communication signals. In this manner, a status indicating that the radiation detector 7 is ready to initiate a radiation detection operation can be delivered from UPB 1 directly to the portable trigger unit (i.e., RF transmitter 17), instead of—or in addition to—computing device 13.

Figure 6A:
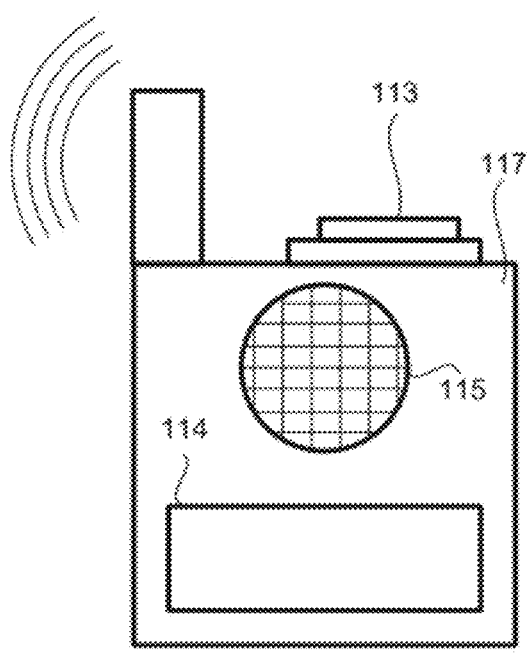
FIG. 6A illustrates a mobile trigger unit that includes a communication unit to inform an operator of a ready state of the radiation detector.

FIG. 6A illustrates an exemplary embodiment of RF transmitter 17, which has been configured as a mobile trigger unit 117. More specifically, a mobile trigger unit 117 can be implemented as a wireless battery-powered hand switch that includes a two-position pushbutton 113 and incorporates within the hand switch itself an "informing unit" that can positively and unequivocally inform the operator that the detector is indeed ready. In certain arrangements, the informing unit of the wireless hand switch takes the form of a display unit 114, such as a LED or LCD panel, or the like. In other arrangements, the information unit may take the form of a haptic interface (not shown) in order to inform the operator of a ready status of the detector by vibration. In further arrangements, the information unit may take the form of a sound emitting unit 115 (e.g., a beep), or the like. In this manner, the operator can effectively and unequivocally be informed that the radiation detector is ready, and can then initiate exposure at the most appropriate time, even if the operator is freely moving or is positioned at a location remote from the computing device 13 or the imaging location.

Figure 6B:
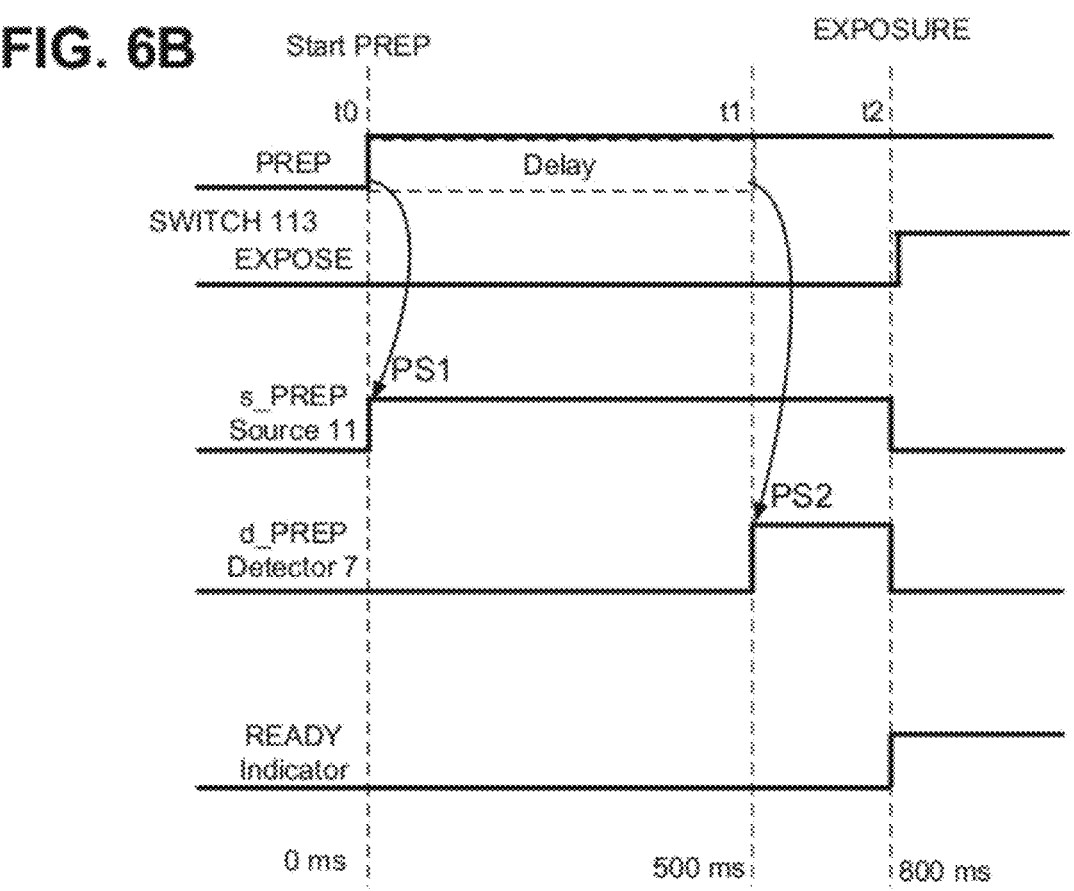
FIG. 6B illustrates a timing diagram for the mobile trigger unit of FIG. 6A.

FIG. 6B illustrates an exemplary timing diagram implemented for exposure control in system 10. In FIG. 6B, when the two-position pushbutton switch 113 is initially pressed by the operator at a time t0 (e.g., t=0 ms), the pushbutton advances to a PREP position (first position) and a first prep signal PS1 is sent from the mobile trigger unit 117 to radiation source 11, via UPB 1, in the manner discussed above in reference to FIGS. 4C and 5. At substantially the same time t0 (i.e., t=0 ms), and in response to the first prep signal PS1, the radiation source 11 initiates a radiation preparation operation (s_PREP). For example, if the radiation source 11 is a portable X-ray generator, the X-ray generator boosts the speed of the rotor to an appropriate speed rate. After a predetermined delay with respect to time t0, at time t1 (e.g., at t=500 ms), a second prep signal PS2 is sent to radiation detector 7, so that the radiation detector 7 initiates a detection preparation operation (d_PREP). For example, the radiation detector 7 is reset so that any charges previously accumulated within the pixels of the detector are "flushed" out. In order to send the second prep signal PS2 to radiation detector 7, and to implement the necessary predetermined delay, a timing circuit based on FIG. 6B can be used within the mobile trigger unit 117 or within the logic circuitry of UPB 1 (see FIG. 4B).

When the s_PREP operation of radiation source 11 and the d_PREP operation of the radiation detector 7 are complete, at a predetermined time t2, an Exposure ready signal is forwarded from UPB 1 to mobile trigger unit 117. More specifically, in this embodiment, UPB 1 is configured to determine whether the preparation operations of the radiation source 11 and radiation detector 7 have been completed. This determination may be accomplished, for example, by board 25 of UPB 1 by monitoring a high/low signal of the voltage supplied to the radiation source 11 and radiation detector 7, respectively. When it is determined that the preparation operations (s_PREP and d_PREP) have been completed, a "ready" signal is sent from UPB 1 to mobile trigger unit 117. Upon receiving the ready signal from UPB 1, at time t2, at least one of the display unit 114 and sound emitting unit 115 is activated so as to communicate to the operator that the radiation detector 7 is ready (READY Indicator). At substantially this time t2 or immediately thereafter, the operator advances the two-position pushbutton 113 to a second position (exposure position), whereby an exposure signal (EXPOSE) is sent from mobile trigger unit 117 to radiation source 11 under the control of UPB 1. That is, once the two-position pushbutton 113 of mobile trigger unit 117 is fully depressed, the portable radiation imaging system 10 can promptly and securely perform an imaging operation even if the operator is positioned away (remote) from computing device 13 and an imaging location (first location 100).

In this embodiment, mobile trigger unit 117 has been implemented as a long-range RF communication unit capable of two-way communication, so that the above described "dead man" switch can be implemented as a wireless hand switch capable of informing to the operator that an exposure trigger signal can be sent to the radiation source 11, in accordance with a "ready" status of radiation detector 7. In this manner, the operator can effectively and timely operate the system 10, even when freely moving from one location to another, or even when positioned at the remote location.

<Second Embodiment>

FIG. 7 schematically shows a portable radiation imaging system 10 in a deployed state, in accordance with a second embodiment of the present invention. In FIG. 7, in order to avoid unnecessary duplication, the components having reference numerals similar to those already described in reference to the first embodiment are not described. In the second embodiment, as illustrated in FIG. 7, the cable C3 that connects radiation source 11 to UPB 1 has been replaced by a wireless link 55 (third wireless link). More specifically, in the second embodiment, radiation source 11 is equipped with a wireless receiver 51 adapted to receive the triggering signal originated from RF transmitter 17. To that end, UPB 1 is operatively connected to an RF transmitter 54 capable of communicating with RF receiver 51. As can be understood, the wireless link 55 can be implemented in a number of manners. For example, wireless link 55 may be implemented as a digital spread spectrum (DSS) link, as an infrared (IR) link, or a communication link under known protocols such as 802.11a/b/g/n or the like.

<Third Embodiment>

Figure 8:
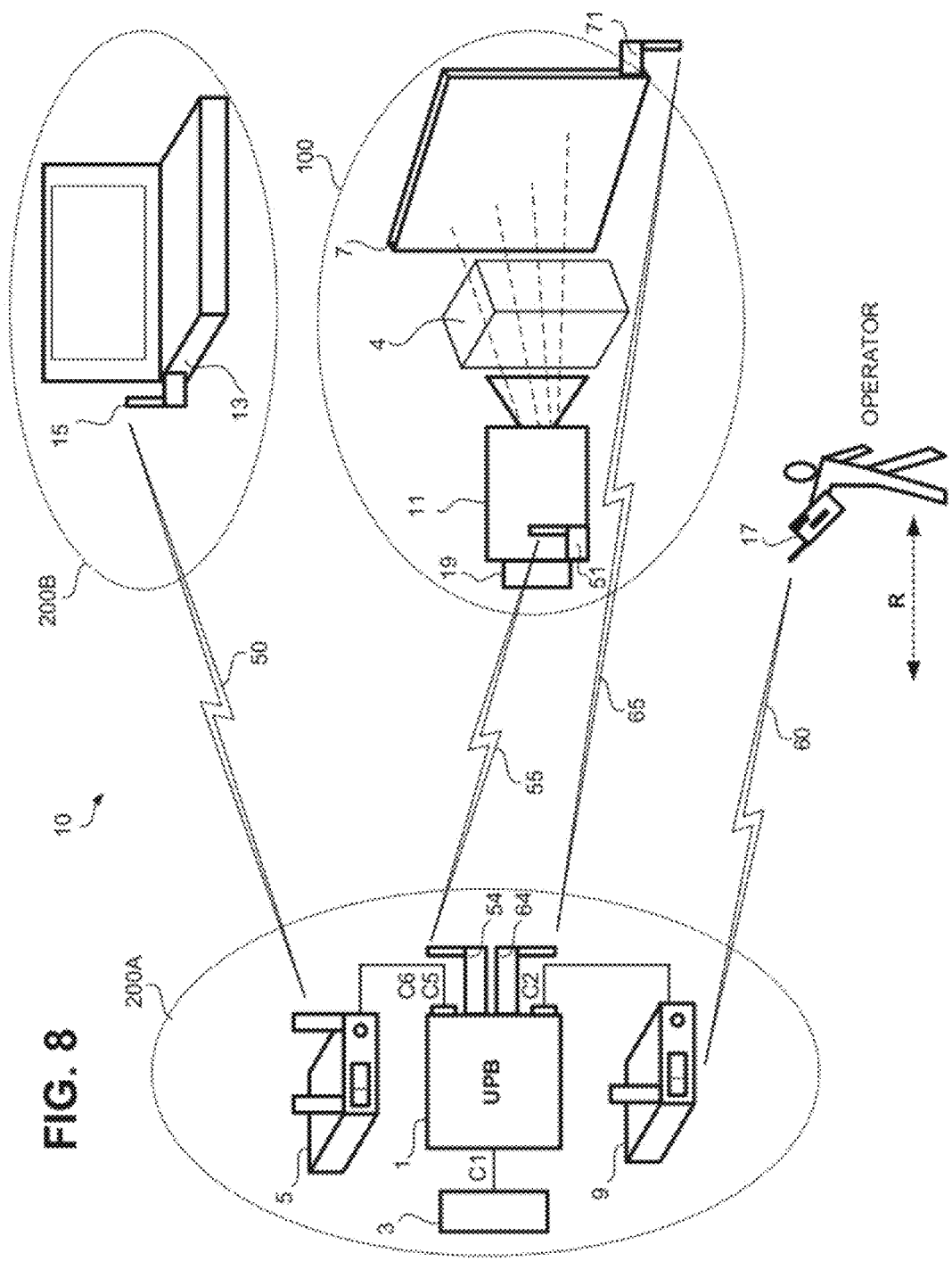
FIG. 8 shows an exemplary arrangement of components of a radiation imaging system in a deployed state, in accordance with a further embodiment of the present invention.

FIG. 8 shows a portable radiation imaging system 10 in a deployed state, in accordance with a third embodiment of the present invention. As described in reference to FIGS. 1 and 7 above, in the first and second embodiments, the radiation detector 7 is operatively connected to UPB 1 via a cable C4. However, in the present embodiment, as illustrated in FIG. 8, cable C4 may be replaced by a wireless link 65 (fourth wireless link). More specifically, the radiation detector 7 may itself include a power source or battery (not shown) and a transceiver 71. In addition, UPB 1 can be provided with a transceiver 64. In this manner, the radiation detector 7 can be wirelessly connected to UPB 1 via a wireless link 65. One example of a wireless radiation detector 7 is Canon® digital radiography detector CXDI-70C, but other wireless detectors can be used. It should be noted by persons of ordinary skill in the art that the fourth wireless link 65 that replaces cable C4 may be easily implemented, for example, as an additional data-transfer link in a manner similar to the first wireless link 50.

Advantageously, in accordance with at least one of the foregoing embodiments, the system 10 described above is designed to be self-contained, lightweight, modular, and portable. Accordingly, with reference again to FIG. 2, UPB 1, power source 3, wireless bridge 5, receiver 9, and a spare power source 3' may be mounted to panel 27 in order to keep the system self-contained and organized. The configuration depicted should not be considered limiting as the arrangement of the components may vary according to the relative size and weight of the components selected. For example, it should be understood that at least wireless bridge 5 and receiver 9 are components that may be implemented within one or more of boards 21, 23 and 25 of UPB 1, or may be implemented as additional boards, residing within housing H of UPB 1. Minimizing the number and size of components of system 10 can advantageously yield a compact and lightweight imaging system that can be easily transported and rapidly deployed.

Figure 9:
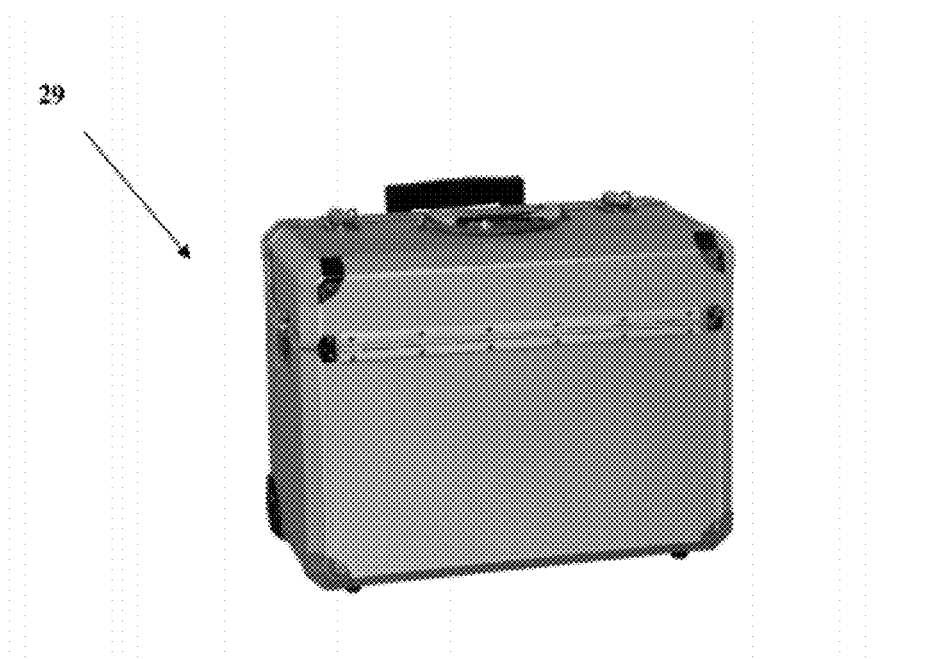
FIG. 9 shows a rolling carrying case that retains components of an experimental prototype of a radiation imaging system in a packaged state, in accordance with an embodiment of the present invention.
Figure 10:
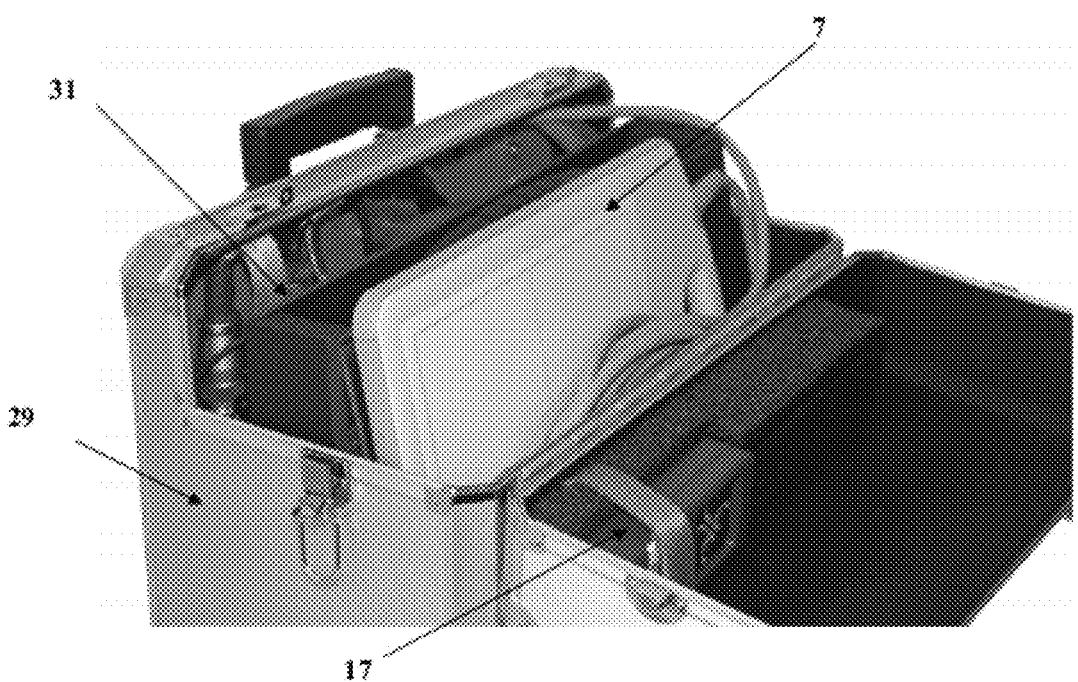
FIG. 10 shows the inside of the rolling carrying case in FIG. 9.
Figure 11:
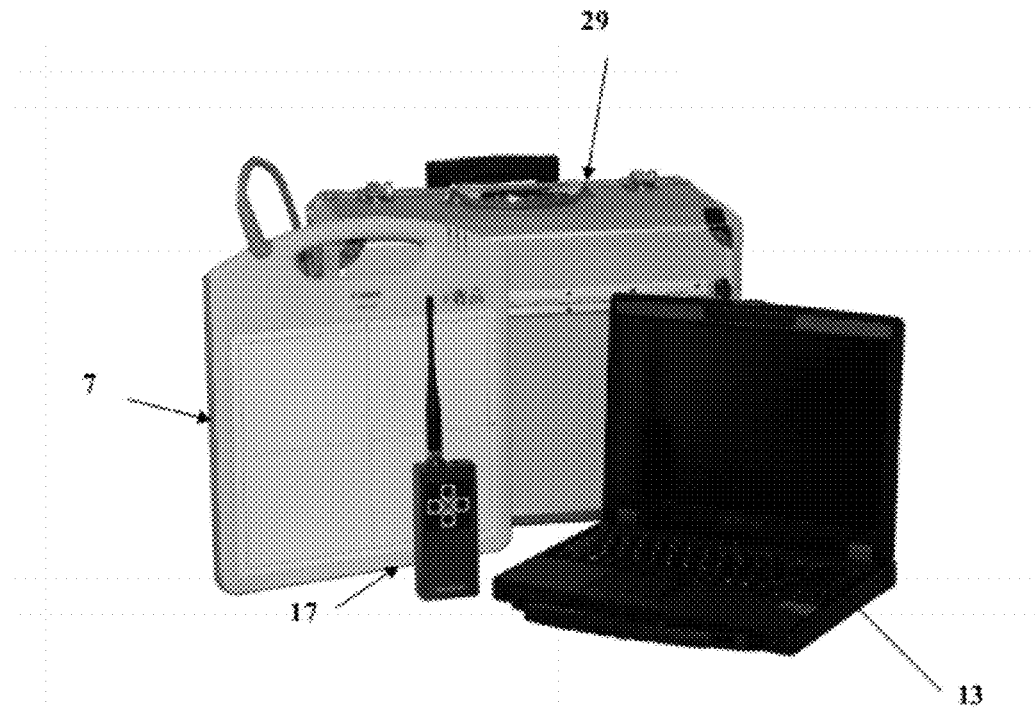
FIG. 11 shows components of an experimental prototype of a radiation imaging system in a ready-to-deploy state.
Figure 12:
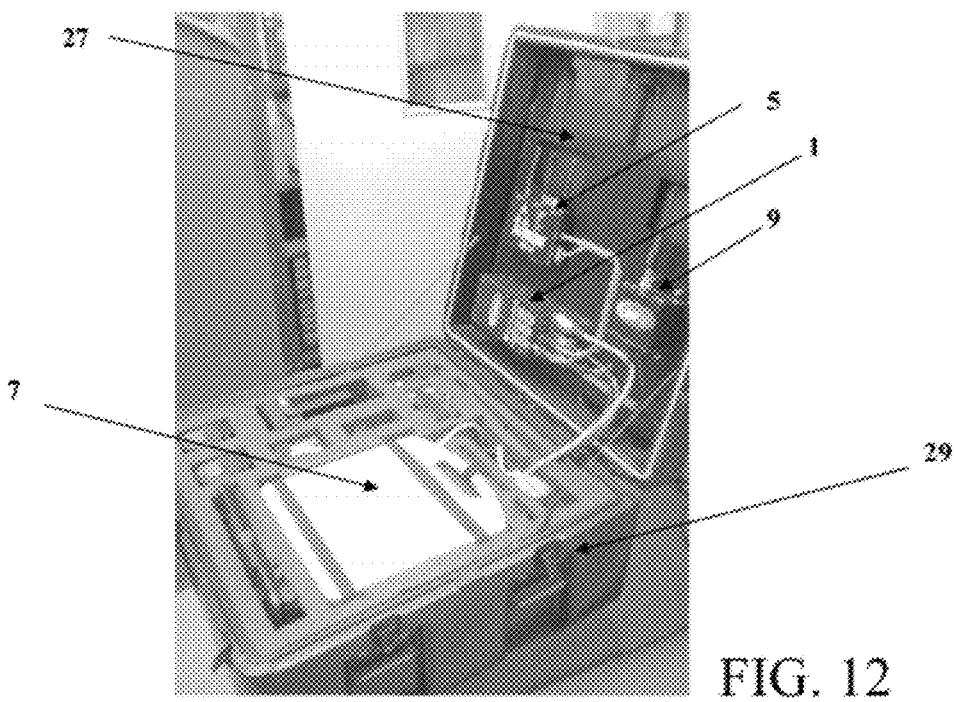
FIG. 12 shows one embodiment of the imaging radiation system assembled in a form-fitted self-contained case, in accordance with an embodiment of the present invention.

FIGS. 9-12 illustrate exemplary arrangements and containers for packing and transporting the above described system 10. FIG. 9 illustrates an exemplary carrier 29. Fig. illustrates carrier 29 in an opened state with components of system 10 contained therein. FIG. 11 exemplary shows carrier 29 next to other components of system 10 to illustrate their relationship in size. FIG. 12 illustrates an alternate embodiment of carrier 29 where panel 27 and components attached thereto (see FIG. 2) have been attached to the cover of carrier 29, while the other components are arranged in a main compartment of carrier 29. Thus, as illustrated in FIGS. 9-12, a rolling carrier 29 may be used to pack and carry the panel 27 along with the radiation detector 7, computing device 13, transmitter 17, and any additional or spare components. In one embodiment, carrier 29 may be a standard padded "pilot's case" having customized form-fitting compartments to securely retain the components of the system 10 in a substantially connected state, as shown in FIG. 12, for easy deployment. In another embodiment, FIG. 10 shows carrier 29 with a slot 31 where the components of system 10 can be securely contained in a substantially unconnected state. Alternatively, the aforementioned components of system 10 may be assembled to fit in a standard backpack, military pack, or other luggage device sufficiently sized to safely contain the components.

Examples of Practical Applications of the Portable Radiation Imaging System

As discussed in the Background section, the use and application of conventional portable imaging systems can be rather limited because an operator is required to be present within the immediate premises where the object is to be imaged because the entire system is often controlled with a single control unit (e.g., a portable computing device). However, in practical applications, for example, when it is necessary to image objects that may be potentially harmful to the operator, the presence of the operator within the area surrounding the object may be undesirable. Alternatively, when imaging other objects, an operator may need to first position an object in an imaging position and repeatedly move to a control area from where the object can be safely imaged. This process is inconvenient for an operator. As disclosed herein, various embodiments are proposed where the operator can efficiently perform imaging operations even when the operator is positioned at a remote location or during movement between locations.

Although in practical applications it may be easier to control the entire imaging system with a single control unit, as it is done in conventional portable imaging systems, the present application advantageously uses a portable trigger unit and components related thereto, for the reasons discussed below. Specifically, wireless components such as wireless bridge 5 and transceiver 15 can be relatively sensitive to interference and could have unstable bandwidth depending on the environment and distance from one another. Sensitivity to interference and bandwidth stability are particularly more important issues for a portable system because environmental conditions can be constantly changing. Accordingly, with respect to the above-described embodiments of present invention, some electronic shielding (e.g., wall, mesh, or the like) may be necessary to prevent surrounding items from reducing the bandwidth of the first wireless link 50 established between wireless bridge 5 and transceiver 15. Notwithstanding these precautions, because wireless bridge 5 is responsible for timely and securely transmitting all of the image data from the radiation detector 7 to computing device 13 via UPB 1, the bandwidth of wireless bridge 5 is likely to be occupied by data-intensive high-resolution and high-quality image data transmission, especially during continuous or dynamic image acquisition.

Sensitivity to interference and bandwidth stability are of particular concern in the case where a portable imaging system may be used for capturing images to be reviewed by medical personnel or investigators who must make judgments regarding medical diagnoses or the existence of dangerous materials, respectively. More specifically, in cases where high-resolution still images or continuous video images with a large number of quantization bits are being transmitted, interference and bandwidth instability may greatly affect the timely transmission of such images. For example, high-resolution still images or continuous video images with a large number of quantization bits may cause delayed communication when using the wireless bridge 5. Further the computing device 13 may operate in a multi-tasked environment and may be occupied by other tasks, for example updating a version of software installed, installing security updates, or processing other communications. Those other tasks of the computing device 13 also may cause delayed communication using the bridge 5. Accordingly, an alternate communication channel (i.e., the second wireless link) is advantageously provided for transmitting time-critical data such as a triggering signal for radiation source 11, which synchronizes radiation timing with the acquisition process of radiation detector 7.

For example, with respect to the above described embodiments, the operator should send control parameters and necessary data for acquiring images, including data for imaging conditions (exposure time, power of radiation, and the like) and identification data (file name, date, name of doctors/inspectors and the like) for each image. Imaging conditions and identification data are not time-critical and can be transmitted from computing device 13 to UPB 1 via the wireless bridge 5 at any time even before the start of an image acquisition process. However, if time-critical parameters, such as triggering and synchronization signals, are to be transmitted from computing device 13 during the time that image data is being transmitted from bridge 5 to computing device 13 or the computing device 13 is largely occupied by the other tasks, there may be some appreciable delay in the transmission of time-critical parameters. In other words, when only the first wireless link 50 is used for image transfer and signal control, significant delay can occur in the image acquisition process.

Moreover, if images are continuously acquired, particularly in situations where the objects to be captured are frequently or continuously moved, triggering of radiation emission from radiation source 11 and image capturing timing may be of high importance in order to acquire desired and/or reliable images. For example, such objects to be captured can be located on a conveyor belt and can be moving relative to the radiation detector 7 and the radiation source 11.

Accordingly, in the embodiments of the present invention, a secondary communication link, namely the RF link between transmitter 17 and receiver 9 (the second wireless link or time-critical link) has been established in order to provide transmission of time-critical triggering and synchronization signals separate from the image-transfer link. It should be understood that although a dedicated RF link has been described for the time-critical link, it would be feasible to utilize a different, less-powerful secondary wireless communication link for transmission of time-critical parameters because the bandwidth requirements are lower than those required for image transfer. By using such a secondary communication link, a user of the system can timely operate the manually operable switches of RF transmitter 17 (or portable trigger unit 117) to send the trigger signal to the receiver 9 while remotely monitoring the position of objects to be imaged.

The foregoing practical example is considered particularly advantageous in applications where imaging of moving objects may be required. In such an environment, computing device 13 would be located in a remote location from the object to be imaged. However, if the object to be imaged moves, it is often necessary for the system operator to change the position and orientation of the detector or radiation source. Alternatively, the operator may need to change the position of the object with respect to radiation source 11 and radiation detector 7. If, as discussed above, the object to be imaged is located at the first location 100 and the computing device 13 is located at a second location remote from the first location, then the operator may need to travel back and forth between the two remote locations, in order to be near computing device 13. In other words, if image acquisition instructions (e.g., triggering and synchronization signaling) are issued exclusively from the location where the computing device is located, the imaging system is constrained to be used within a limited area. However, as described above, a mobile trigger unit in the form of a remote wireless unit (e.g., RF transmitter 17) allows the operator to trigger the imaging system 10 from any location (including a location remote from the computing device and remote from the imaging location), even if the operator is in active movement. That is, the operator can activate the radiation source from the vicinity of the object being imaged, even if the computing device 13 is located at a remote location. For example, when operating upon a moving object, the operator can first enter the imaging information (see step S108 in FIG. 5) and then move to the position where the object is located. Once the relative position of the object to be imaged is adjusted by the operator, e.g., with respect to radiation source 11 and radiation detector 7, the operator can immediately trigger the image acquisition process by using the RF transmitter 17. In this situation, the image data can be transmitted from radiation detector 7 to computing device 13 via UPB 1 even before the operator can return to the location where computing device 13 is located.

Accordingly, the use of a time-critical link separate from, and in addition to, an image-transfer link can reduce the time needed to acquire a series of images, and can advantageously improve utilization of the portable imaging system disclosed herein. Moreover, the use of a mobile trigger unit configured in the conventional "dead man" switch manner, and equipped with an informing unit, can enable the operator to receive an indication of a time when the radiation detector is ready to initiate a radiation detection operation, even if the operator is moving or positioned in a remote location.

Figure 13:
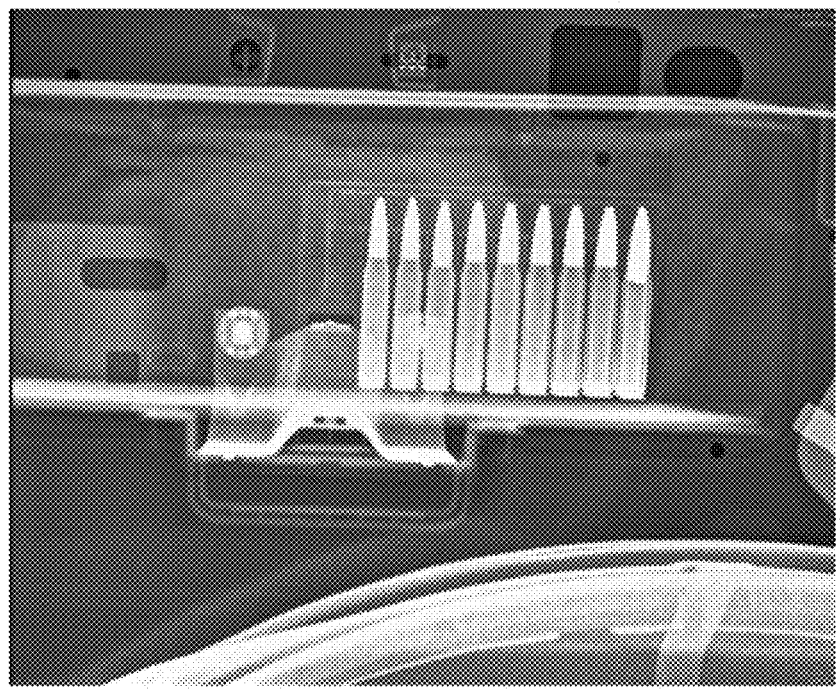
FIGS. 13-15 are examples of images acquired using at least one embodiment of the imaging system and method thereof described herein.
Figure 14:
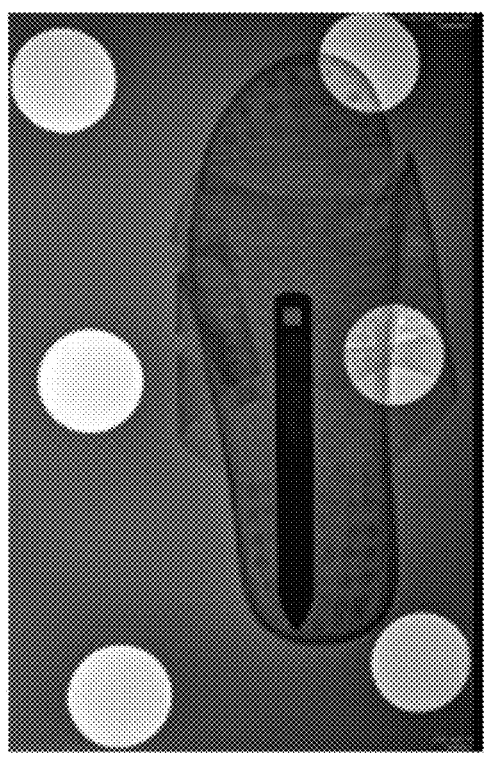
Figure 15:
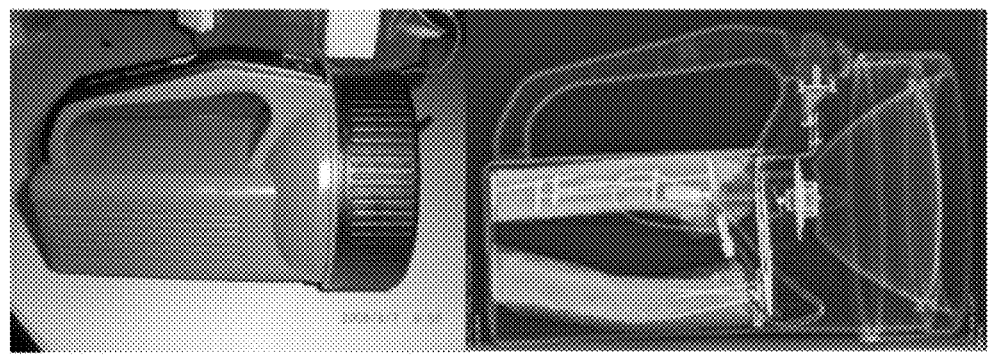

FIGS. 13-15 are examples of images acquired using at least one embodiment of the imaging system and method thereof described herein. FIG. 13 illustrates, for example, contraband contents imaged within the structure of an automobile during routing inspection at a remote check point. FIG. 14 illustrates and example of imaging an object while moving on a conveyor belt. Specifically, FIG. 14 illustrates an image of footwear imaged during routing inspection at a check point, such as an airport or building entrance. FIG. 15 is an exemplary image of an object containing therein potentially harmful explosives.

Table 1 shown below illustrates exemplary features and specifications for one embodiment of the radiation imaging system described herein and used to generate the exemplary images of FIGS. 13-15.

TABLE 1

| Exemplary Features and Specifications | |
|---|---|
| STANDARD COMPONENTS | |
| X-ray Generator (XR200) | 4 Channel Handheld Transmitter - RF |
| Rugged Touchscreen Laptop | 4 Channel Receiver - RF |
| Canon ® CXDI ® Digital Flat Panel | Second/Spare Generator Battery |
| Universal Power Box Wireless Capability | Battery Charger |
| X-RAY SOURCE | |
| X-Ray Source (XRS200) | 150 kV, |
| Size | 12.5" (31.75 cm) × 4.5" (11.5 cm) × 7.5" (19 cm). |
| Weight | 12 lbs (5.5 kg) with battery |
| Power Supply | DeWalt 14.4 V rechargeable, nickel cadmium battery; 3000 pulses per battery charge |
| Battery Recharge Time | 1 hour with standard DeWalt charger; 15 minute charger available |
| Output Dose | 3mR per pulse at 1 ft. (30 cm) with filtration equivalent to 2.5 mm of aluminum |
| Pulse Rate | 25 pulses per second nominal |
| Pulse Length | 50 nanoseconds |
| Maximum Pulse | 300 pulses per hour |

TABLE 1-continued

| Exemplary Features and Specifications | | |
|---|---|---|
| Penetration | (15 mm) steel | |
| DIGITAL DETECTOR (choice) | | |
| Model Name(s) | CXDI-60GI | CXDI-50GI |
| Scintillator | GOS (Gadolinium Oxysulfide) | GOS |
| Pixel Pitch | 160 microns | 160 microns |
| Pixels | 2.6 mil | 5.9 mil |
| Imaging Size | up to 9" × 11" in (23 × 28 cm) | up to 14" × 17" in (35 × 43 cm) |
| A/D | 14-bit | 14-bit |
| Grayscale | 4096 (12-bit) | 4096 (12-bit) |
| Interface | DICOM 3.0 | DICOM 3.0 |
| Preview Image Access Time | approx. 3-5 seconds | approx. 3-5 seconds |
| Weight | 5.9 lbs (2.7 kg) | 10.6 lbs (4.8 kg) |
| LAPTOP | | |
| CPU | Intel ® Core ™ 2 Duo T7200 2.0 GHz processor | |
| Memory | 1 GB DDR2 expandable to 2 GB | |
| Operating System | Genuine Windows ® XP Professional | |
| Storage | SATA 120 GB expandable to 160 GB | |
| VGA Controller | Integrated in Intel ® 945GM, 128 MB shared memory | |
| Display | 14.1" WXGA (1280 × 800) TFT LCD Optional touch screen Optional sunlight readable display | |
| OPTIONS | | |
| X-Ray Source (XRS-3) | 300 kV, 12 lbs (5.5 kg), Penetration: (25 mm) steel | |
| Deployment Configuration | Rugged Case(s), Backpack, or Custom | |
| Power | AC/DC or Battery | |

It will be understood that the embodiments of the present invention have been disclosed by way of example only and that other modifications and alterations may occur to those skilled in the art without departing from the spirit and scope of the invention herein. The scope of the following claims is to be accorded the broadest reasonable interpretation so as to encompass all modifications that include equivalent structures and functions thereof.

The invention claimed is:

1. A portable x-ray imaging system, comprising:
a x-ray source configured to irradiate an object with x-ray radiation;
a x-ray detector configured to detect the x-ray radiation passing through the object and to generate image data based on detected x-ray radiation;
a computing device configured to receive and process the image data-generated by the x-ray detector to produce an x-ray image;
a radio frequency (RF) trigger unit configured to emit a trigger signal to remotely initiate a x-ray imaging operation; and
a universal power box having a housing enclosure and configured to receive electric power from an alternate current (AC) power source and/or a direct current (DC) power source and configured to generate DC voltage to power at least one of a first power board, a second power board and a logical interface board disposed as floating boards within the housing enclosure,
wherein the logical interface board includes logical circuitry configured to (a) receive the trigger signal from the RF trigger unit via RF wireless communication, (b) transfer the trigger signal to the x-ray source and to the x-ray detector via wired or wireless communication, (c) receive the image data from the x-ray detector via wired or wireless communication, and (d) transfer the image data received from the x-ray detector to the computing device via digital wireless communication, wherein, in response to receiving the trigger signal from the RF trigger unit, the logical data interface routes the trigger signal to the x-ray source and to the x-ray detector to initiate the imaging operation, and wherein the x-ray source, the x-ray detector, the computing device, the universal power box, and the RF trigger unit are configured to be removably housed in a portable housing having the shape of a suitcase.

2. The portable x-ray imaging system according to claim 1, wherein the universal power box includes a first output port configured to supply the trigger signal to the x-ray source via a first cable, and a second output port configured to supply a DC voltage and the trigger signal to the x-ray detector via a second cable.

3. The portable x-ray imaging system according to claim 1, further comprising a wireless bridge operatively connected to the universal power box and a wireless transceiver operatively connected to the computing device, wherein the logical interface board transfers the image data received from the x-ray detector to the computing device via wireless communication through a wireless communication link established between the wireless bridge and the wireless transceiver.

4. The portable x-ray imaging system according to claim 1, further comprising an RF transceiver operatively connected to the universal power box, wherein the logical interface board receives the trigger signal from the RF trigger unit via RF wireless communication through an RF wireless link established between the RF transceiver and the RF trigger unit.

5. The portable x-ray imaging system according to claim 1, wherein the RF trigger unit includes a long-range, multi-channel, digitally encoded handheld RF switch.

6. The portable x-ray imaging system according to claim 1, wherein the RF trigger unit is configured to receive notification of a time when the x-ray detector is ready to start detecting the x-ray radiation.

7. The portable x-ray imaging system according to claim 6, wherein the RF trigger unit includes a two-position switch configured to activate the radiation source to emit x-ray radiation only after receiving the notification that the radiation detector is ready to detect radiation.

8. The portable x-ray imaging system according to claim 1, wherein the logical interface board includes logic circuitry configured to control the flow of data such that the trigger signal from the RF trigger unit is transferred to the x-ray source with higher priority than the image data transferred from the x-ray detector to the computing device.

9. The portable x-ray imaging system according to claim 1, wherein the universal power box communicates with the x-ray source through a first wired link to transfer the trigger signal to the x-ray source via wired communication, and wherein the universal power box communicates with the x-ray detector through a second wired link to transfer the trigger signal and to receive the image data from x-ray detector via wired communication.

10. The portable x-ray imaging system according to claim 1, wherein the x-ray source is a battery-powered wireless x-ray generator and the x-ray detector is a battery-powered wireless x-ray detector, wherein the universal power box communicates with the battery-powered wireless x-ray generator through a third wireless link to transfer the trigger signal thereto via wireless communication, and wherein the universal power box communicates with the battery-powered wireless x-ray detector through a fourth wireless link to transfer the trigger signal and to receive the image data via wireless communication.

11. The portable x-ray imaging system according to claim 1, wherein the universal power box includes a first input port for connecting to the AC power source and a second input port for connecting to the DC power source, and a plurality of output ports for providing DC voltage to at least one of the x-ray source and the x-ray detector.

12. The portable x-ray imaging system according to claim 1, wherein the x-ray source, the x-ray detector, the computing device, the universal power box and the RF trigger unit are removable from the suitcase, and deployable such that the x-ray source and the x-ray detector are placed at a first location, the computing device is placed at a second location remote from the first location, and the RF trigger unit is operable by a user located remote from the first and second locations.

* * * * *